United States Patent
Stelzer

(10) Patent No.: US 8,933,048 B2
(45) Date of Patent: Jan. 13, 2015

(54) METHODS OF TREATING CARDIOMYOPATHY

(71) Applicant: Case Western Reserve University, Cleveland, OH (US)

(72) Inventor: Julian E. Stelzer, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 13/624,421

(22) Filed: Sep. 21, 2012

(65) Prior Publication Data

US 2013/0072549 A1 Mar. 21, 2013

Related U.S. Application Data

(60) Provisional application No. 61/537,425, filed on Sep. 21, 2011.

(51) Int. Cl.
*A61K 48/00* (2006.01)
*A01N 63/00* (2006.01)
*A61K 31/7088* (2006.01)

(52) U.S. Cl.
CPC .................................. *A61K 31/7088* (2013.01)
USPC ........................................ 514/44 R; 424/93.1

(58) Field of Classification Search
None
See application file for complete search history.

(56) References Cited

U.S. PATENT DOCUMENTS

2004/0086876 A1 5/2004 Seidman

OTHER PUBLICATIONS

Merkulov, S. et al., "In vivo cardiac myosin binding protein c gene transfer rescues myofilament contractile dysfunction in cardiac myosin binding protein c null mice", Circ Heart Fail, Sep. 2012, pp. 638-644.*
Stelzer, Julian, et al., "Effects of low-level α-myosin heavy chain expression on contractile kinetics in porcine myocardium", Am J Physiol Heart Circ Physiol. Mar. 2011; 300(3): H869-H878.
Stelzer, Julian, et al., "Acceleration of Stretch Activation in Murine Myocardium due to Phosphorylation of Myosin Regulatory Light Chain" J. Gen. Physiol, The Rockefeller University Press, vol. 128, No. 3, Sep. 2006, pp. 261-272.
Stelzer, Julian, et al., "Ablation of Cardiac Myosin-Binding Protein-C Accelerates Stretch Activation in Murine Skinned Myocardium", Circ. Res. 2006;98:1212-1218.
Stelzer, Julian, et al., "Ablation of Myosin-Binding Protein-C Accelerated Force Development in Mouse Myocardium", Biophysical Journal, vol. 90, Jun. 2006, pp. 4119-4127.
Stelzer, Julian, et al., Activation Dependence of Stretch Activation in Mouse Skinned Myocardium: Implications for Ventricular Function,
J. Gen. Physiol., The Rockefeller University Press, vol. 127, No. 2, Feb. 2006, pp. 95-107.
Chen, Yong, et al., "Altered in vivo left ventricular torsion and principal strains in hypothyroid rats", Am. J. Physiol Heart Circ. Physiol 299:H1577-H1587, 2010.
Locher, Matthew R., "Determination of rate constants for tunrover of myosin isioforms in rat myocardium: implication for in vivo contractile kinetics", Am J. Physiol Heart Circ Physiol 297: H247-H256, 2009.
Tong, Carl W., "Acceleration of Crossbridge Kinetics by Protein Kinase a Phosphorylation of Cardiac Myosin Binding Protein C Modulates Cardiac Function", Circ Res. 2008;103:974-982.
Stelzer, Julian E., et al., "Transmural variation in myosin heavy chain isoform expression modulates the timing of myocardial force generation in porcine left ventricle", J Physiol 586.21 (2008) pp. 5203-5214.
Stelzer, Julian E., et al., "Differential Roles of Cardiac Myosin-Binding Protein C and Cardiac Troponin I in the Myofibrillar Force Responses to Protein Kinase A Phosphorylation", Circ. Res. 2007;101:503-511.
Stelzer, Julian E., et al., "Role of myosin heavy chain composition in the stretch activation respose of rat myocardium", J Physiol 579-1 (2007) pp. 161-173.
Stelzer, Julian E., et al., "Contributions of Stretch Activation to Length-dependent Contraction in Murine Myocardium", J. Gen. Physiol., The Rockefeller University Press, vol. 128, No. 4, Oct. 2006, pp. 461-471.
Stelzer, Julian E., et al., "Protein Kinase A-Mediated Acceleration of the Stretch Activation Response in Murine Skinned Myocardium is Eliminated by Ablation of cMyBP-C", Circ. Res. 2006;99:884-890.
Malik, Fady I., et al., "Cardiac Myosin Activation: A Potential Therapeutic Approach for Systolic Heart Failure", Science, vol. 331, Mar. 18, 2011, pp. 1439-1443.
Jia, Weitao, et al. "Identification of Novel Protein Kinase A Phosphorylation Sites in the M-domain of Human and Murine Cardiac Myosin Binding Protein-C Using Mass Spectrometry Analysis", J. Proteome Res. 2010, Apr. 5, 2010; 9 (4):1843-1853.
Ge, Ying, et al., "Top-Down high-resolution mass spectrometry of cardiac myosin binding protein C revealed that truncation alters protein phosporylation state", PNAS, Aug. 4, 2009, vol. 106, No. 31, pp. 12658-12663.
Sadayappan, Sakthivel, et al., "A Critical Function for Ser-282 in Cardiac Myosin Binding Protein-C Phosphorylation and Cardiac Function", Circ. Res. Jul. 8, 2011; 109(2): 141-150.
Sadayappan, Sakthivel, et al., "Cardiac Myosin Protein-C Phosphorylation and Cardiac Function", Circ. Res. Nov. 25, 2005; 97(11): 1156-1163.
Sadayappan, Sakthivel, et al., "Cardiac Myosin Binding Protein C Phosphorylation is Cardioprotective", PNAS Nov. 7, 2006, vol. 103, No. 45, pp. 16918-16923.
Desjardins, Candida L., et al. "Cardiac Myosin Binding Protein C Insufficiency Leads to Early Onset of Mechanical Dysfunction", Circ. Cardiovasc Imagin. 2012;5:127-139, Dec. 7, 2011.

* cited by examiner

*Primary Examiner* — Michael Burkhart
(74) *Attorney, Agent, or Firm* — Tarolli, Sundheim, Covell & Tummino LLP

(57) ABSTRACT

A method of treating a cardiomyopathy in a subject includes administering to the subject a therapeutically effective amount of an agent that modulates contractile function in myocardial tissue of the subject.

4 Claims, 8 Drawing Sheets

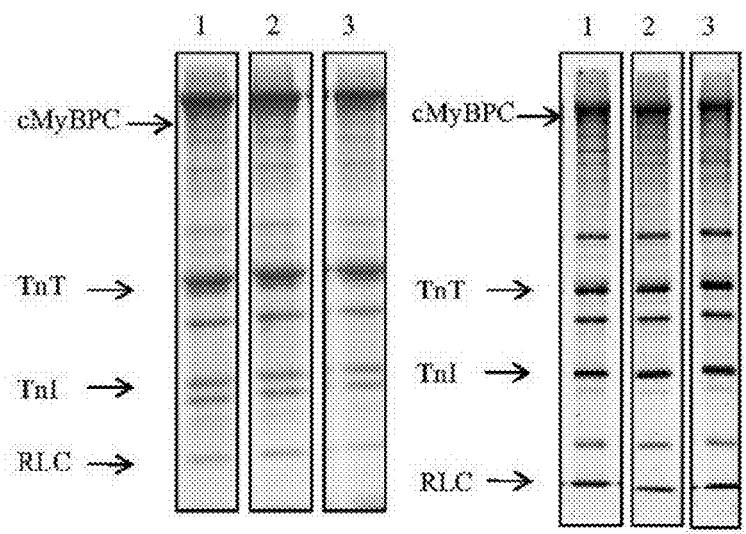
Fig. 1
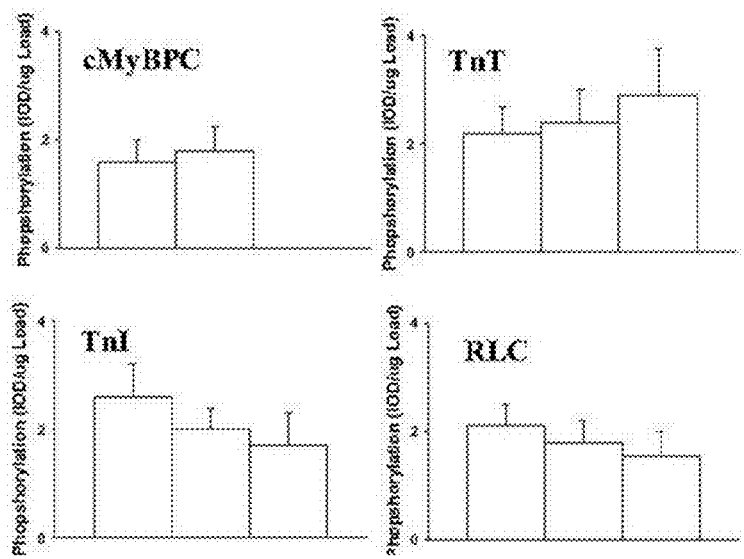
Fig. 2
Figs. 3A-B

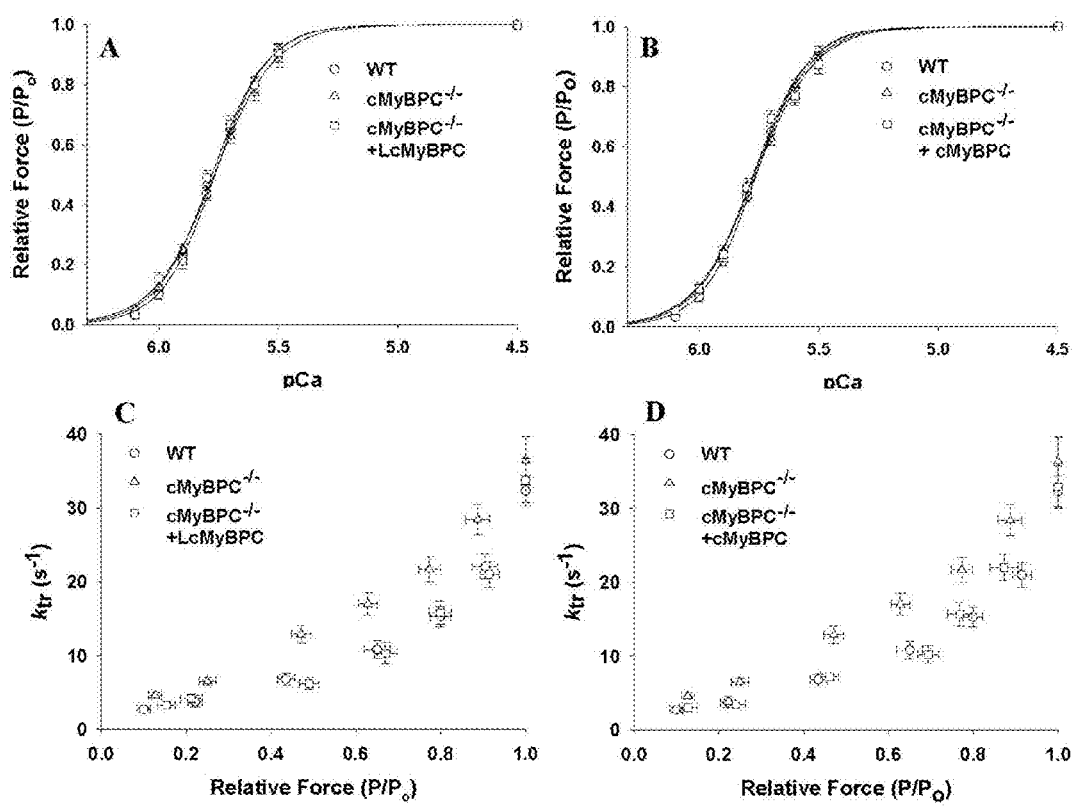
Figs. 6A-D

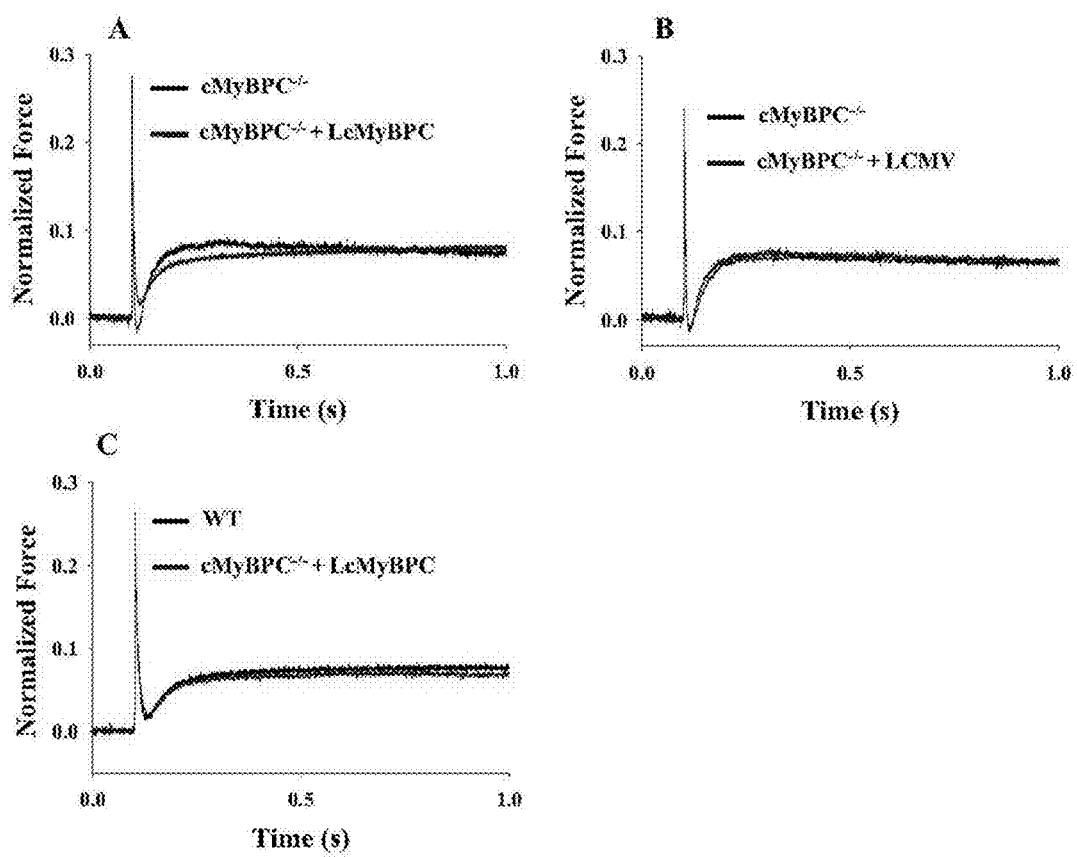
Figs. 7A-C

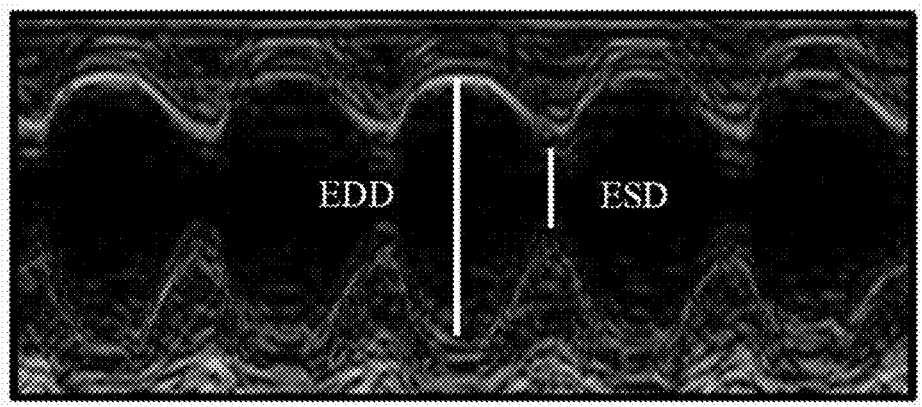
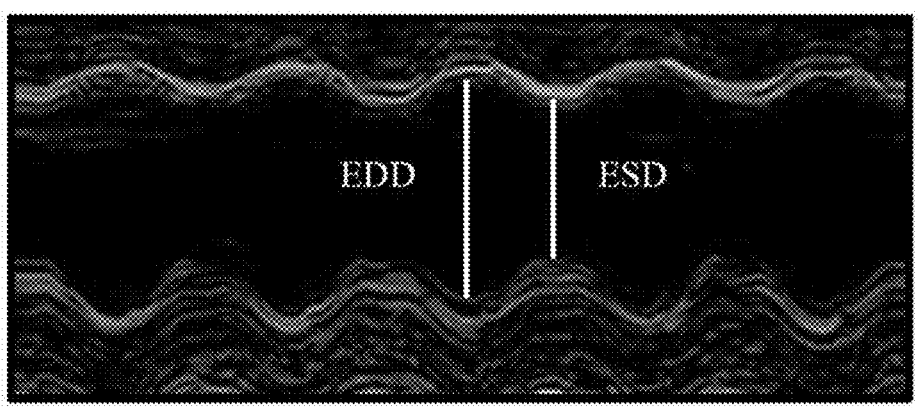
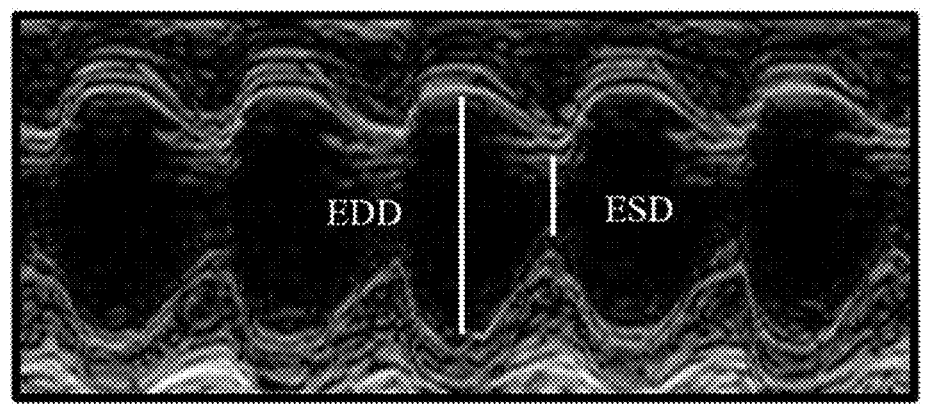
Figs. 8A-C

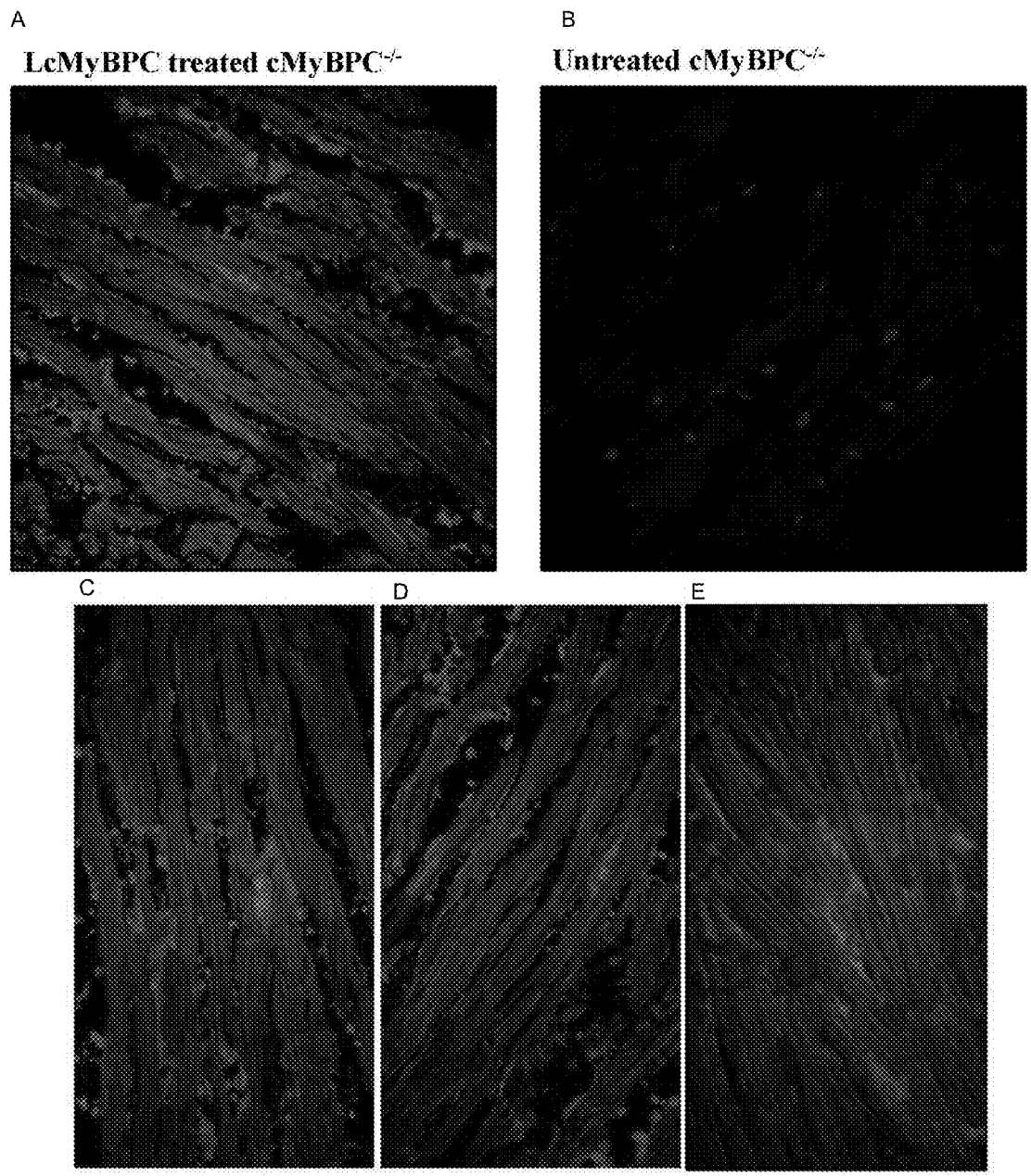
Figs. 10A-E

SEQUENCE LISTING

```
<160> NUMBER OF SEQ ID NOS: 10

<210> SEQ ID NO 1
<211> LENGTH: 1810
<212> TYPE: PRT
<213> ORGANISM: Mus musculus

<400> SEQUENCE: 1

Met Pro Gly Val Thr Val Leu Lys Met Pro Glu Pro Gly Lys Lys Pro
1               5                   10                  15

Val Ser Ala Phe Asn Lys Lys Pro Arg Ser Ala Glu Val Thr Ala Gly
            20                  25                  30

Ser Ala Ala Val Phe Glu Ala Glu Thr Glu Arg Ser Gly Val Lys Val
        35                  40                  45

Arg Trp Gln Arg Asp Gly Ser Asp Ile Thr Ala Asn Asp Lys Tyr Gly
    50                  55                  60

Leu Ala Ala Glu Gly Lys Arg His Thr Leu Thr Val Arg Asp Ala Ser
65                  70                  75                  80

Pro Asp Asp Gln Gly Ser Tyr Ala Val Ile Ala Gly Ser Ser Lys Val
                85                  90                  95

Lys Phe Asp Leu Lys Val Thr Glu Pro Ala Pro Glu Lys Ala Glu
            100                 105                 110

Ser Glu Val Ala Pro Gly Ala Pro Lys Glu Val Pro Ala Pro Ala Thr
        115                 120                 125

Glu Leu Glu Glu Ser Val Ser Ser Pro Glu Gly Ser Val Ser Val Thr
    130                 135                 140

Gln Asp Gly Ser Ala Ala Glu His Gln Gly Ala Pro Asp Asp Pro Ile
145                 150                 155                 160

Gly Leu Phe Leu Met Arg Pro Gln Asp Gly Glu Val Thr Val Gly Gly
                165                 170                 175

Ser Ile Val Phe Ser Ala Arg Val Ala Gly Ala Ser Leu Leu Lys Pro
            180                 185                 190

Pro Val Val Lys Trp Phe Lys Gly Lys Trp Val Asp Leu Ser Ser Lys
        195                 200                 205

Val Gly Gln His Leu Gln Leu His Asp Ser Tyr Asp Arg Ala Ser Lys
    210                 215                 220

Val Tyr Leu Phe Glu Leu His Ile Thr Asp Ala Gln Thr Thr Ser Ala
225                 230                 235                 240

Gly Gly Tyr Arg Cys Glu Val Ser Thr Lys Asp Lys Phe Asp Ser Cys
                245                 250                 255

Asn Phe Asn Leu Thr Val His Glu Ala Ile Gly Ser Gly Asp Leu Asp
            260                 265                 270

Leu Arg Ser Ala Phe Arg Arg Thr Ser Leu Ala Gly Ala Gly Arg Arg
        275                 280                 285

Thr Ser Asp Ser His Glu Asp Ala Gly Thr Leu Asp Phe Ser Ser Leu
    290                 295                 300
```

-continued

Leu Lys Lys Arg Asp Ser Phe Arg Arg Asp Ser Lys Leu Glu Ala Pro
305                 310                 315                 320

Ala Glu Glu Asp Val Trp Glu Ile Leu Arg Gln Ala Pro Pro Ser Glu
                325                 330                 335

Tyr Glu Arg Ile Ala Phe Gln His Gly Val Thr Asp Leu Arg Gly Met
                340                 345                 350

Leu Lys Arg Leu Lys Gly Met Lys Gln Asp Glu Lys Lys Ser Thr Ala
            355                 360                 365

Phe Gln Lys Lys Leu Glu Pro Ala Tyr Gln Val Asn Lys Gly His Lys
370                 375                 380

Ile Arg Leu Thr Val Glu Leu Ala Asp Pro Asp Ala Glu Val Lys Trp
385                 390                 395                 400

Leu Lys Asn Gly Gln Glu Ile Gln Met Ser Gly Ser Lys Tyr Ile Phe
                405                 410                 415

Glu Ser Val Gly Ala Lys Arg Thr Leu Thr Ile Ser Gln Cys Ser Leu
                420                 425                 430

Ala Asp Asp Ala Ala Tyr Gln Cys Val Val Gly Gly Glu Lys Cys Ser
            435                 440                 445

Thr Glu Leu Phe Val Lys Glu Pro Pro Val Leu Ile Thr Arg Ser Leu
450                 455                 460

Glu Asp Gln Leu Val Met Val Gly Gln Arg Val Glu Phe Glu Cys Glu
465                 470                 475                 480

Val Ser Glu Glu Gly Ala Gln Val Lys Trp Leu Lys Asp Gly Val Glu
                485                 490                 495

Leu Thr Arg Glu Glu Thr Phe Lys Tyr Arg Phe Lys Lys Asp Gly Arg
                500                 505                 510

Lys His His Leu Ile Ile Asn Glu Ala Thr Leu Glu Asp Ala Gly His
            515                 520                 525

Tyr Ala Val Arg Thr Ser Gly Gly Gln Ser Leu Ala Met Pro Glu Pro
530                 535                 540

Gly Lys Lys Pro Val Ser Ala Phe Asn Lys Pro Arg Ser Ala Glu
545                 550                 555                 560

Val Thr Ala Gly Ser Ala Ala Val Phe Glu Ala Gly Thr Glu Arg Ser
                565                 570                 575

Gly Val Lys Val Arg Trp Gln Arg Asp Gly Ser Asp Ile Thr Ala Asn
                580                 585                 590

Asp Lys Tyr Gly Leu Ala Ala Glu Gly Lys Arg His Thr Leu Thr Val
            595                 600                 605

Arg Asp Ala Ser Pro Asp Asp Gln Gly Ser Tyr Ala Val Ile Ala Gly
610                 615                 620

Ser Ser Lys Val Lys Phe Asp Leu Lys Val Thr Glu Pro Ala Pro Pro
625                 630                 635                 640

Glu Lys Ala Glu Ser Glu Val Ala Pro Gly Ala Pro Lys Glu Val Pro
                645                 650                 655

Ala Pro Ala Thr Glu Leu Glu Glu Ser Val Ser Ser Pro Glu Gly Ser
                660                 665                 670

Val Ser Val Thr Gln Asp Gly Ser Ala Ala Glu His Gln Gly Ala Pro
            675                 680                 685

Asp Asp Pro Ile Gly Leu Phe Leu Met Arg Pro Gln Asp Gly Glu Val
690                 695                 700

Thr Val Gly Gly Ser Ile Val Phe Ser Ala Arg Val Ala Gly Ala Ser
705                 710                 715                 720

Leu Leu Lys Pro Pro Val Val Lys Trp Phe Lys Gly Lys Trp Val Asp

-continued

```
                725                 730                 735
Leu Ser Ser Lys Val Gly Gln His Leu Gln Leu His Asp Ser Tyr Asp
            740                 745                 750
Arg Ala Ser Lys Val Tyr Leu Phe Glu Leu His Ile Thr Asp Ala Gln
            755                 760                 765
Thr Thr Ser Ala Gly Gly Tyr Arg Cys Glu Val Ser Thr Lys Asp Lys
            770                 775                 780
Phe Asp Ser Cys Ser Phe Asn Leu Thr Val His Glu Ala Ile Gly Ser
785                 790                 795                 800
Gly Asp Leu Asp Leu Arg Ser Ala Phe Arg Arg Thr Ser Leu Ala Gly
                805                 810                 815
Ala Gly Arg Arg Thr Ser Asp Ser His Glu Asp Ala Gly Thr Leu Asp
            820                 825                 830
Phe Ser Ser Leu Leu Lys Lys Arg Asp Ser Phe Arg Arg Asp Ser Lys
            835                 840                 845
Leu Glu Ala Pro Ala Glu Glu Asp Val Trp Glu Ile Leu Arg Gln Ala
            850                 855                 860
Pro Pro Ser Glu Tyr Glu Arg Ile Ala Phe Gln His Gly Val Thr Asp
865                 870                 875                 880
Leu Arg Gly Met Leu Lys Arg Leu Lys Gly Met Lys Gln Asp Glu Lys
                885                 890                 895
Lys Ser Thr Ala Phe Gln Lys Leu Glu Pro Ala Tyr Gln Val Asn
            900                 905                 910
Lys Gly His Lys Ile Arg Leu Thr Val Glu Leu Ala Asp Pro Asp Ala
            915                 920                 925
Glu Val Lys Trp Leu Lys Asn Gly Gln Glu Ile Gln Met Ser Gly Ser
            930                 935                 940
Lys Tyr Ile Phe Glu Ser Val Gly Ala Lys Arg Thr Leu Thr Ile Ser
945                 950                 955                 960
Gln Cys Ser Leu Ala Asp Asp Ala Ala Tyr Gln Cys Val Val Gly Gly
                965                 970                 975
Glu Lys Cys Ser Thr Glu Leu Phe Val Lys Glu Pro Pro Val Leu Ile
            980                 985                 990
Thr Arg Ser Leu Glu Asp Gln Leu Val Met Val Gly Gln Arg Val Glu
            995                1000                1005
Phe Glu Cys Glu Val Ser Glu Glu Gly Ala Gln Val Lys Trp Leu
        1010                1015                1020
Lys Asp Gly Val Glu Leu Thr Arg Glu Glu Thr Phe Lys Tyr Arg
        1025                1030                1035
Phe Lys Lys Asp Gly Arg Lys His His Leu Ile Ile Asn Glu Ala
        1040                1045                1050
Thr Leu Glu Asp Ala Gly His Tyr Ala Val Arg Thr Ser Gly Gly
        1055                1060                1065
Gln Ser Leu Ala Glu Leu Ile Val Gln Glu Lys Lys Leu Glu Val
        1070                1075                1080
Tyr Gln Ser Ile Ala Asp Leu Ala Val Gly Ala Lys Asp Gln Ala
        1085                1090                1095
Val Phe Lys Cys Glu Val Ser Asp Glu Asn Val Arg Gly Val Trp
        1100                1105                1110
Leu Lys Asn Gly Lys Glu Leu Val Pro Asp Asn Arg Ile Lys Val
        1115                1120                1125
Ser His Ile Gly Arg Val His Lys Leu Thr Ile Asp Asp Val Thr
        1130                1135                1140
```

```
Pro Ala Asp Glu Ala Asp Tyr Ser Phe Val Pro Glu Gly Phe Ala
    1145            1150                1155

Cys Asn Leu Ser Ala Lys Leu His Phe Met Glu Val Lys Ile Asp
    1160            1165                1170

Phe Val Pro Arg Gln Glu Pro Pro Lys Ile His Leu Asp Cys Pro
    1175            1180                1185

Gly Ser Thr Pro Asp Thr Ile Val Val Val Ala Gly Asn Lys Leu
    1190            1195                1200

Arg Leu Asp Val Pro Ile Ser Gly Asp Pro Ala Pro Thr Val Val
    1205            1210                1215

Trp Gln Lys Thr Val Thr Gln Gly Lys Lys Ala Ser Thr Gly Pro
    1220            1225                1230

His Pro Asp Ala Pro Glu Asp Ala Gly Ala Asp Glu Glu Trp Val
    1235            1240                1245

Phe Asp Lys Lys Leu Leu Cys Glu Thr Glu Gly Arg Val Arg Val
    1250            1255                1260

Glu Thr Thr Lys Asp Arg Ser Val Phe Thr Val Glu Gly Ala Gly
    1265            1270                1275

Lys Glu Asp Glu Gly Val Tyr Thr Val Thr Val Lys Asn Pro Val
    1280            1285                1290

Gly Glu Asp Gln Val Asn Leu Thr Val Lys Val Ile Asp Val Pro
    1295            1300                1305

Asp Ala Pro Ala Ala Pro Lys Ile Ser Asn Val Gly Glu Asp Ser
    1310            1315                1320

Cys Thr Val Gln Trp Glu Pro Pro Ala Tyr Asp Gly Gly Gln Pro
    1325            1330                1335

Val Leu Gly Tyr Ile Leu Glu Arg Lys Lys Lys Lys Ser Tyr Arg
    1340            1345                1350

Trp Met Arg Leu Asn Phe Asp Leu Leu Arg Glu Leu Ser His Glu
    1355            1360                1365

Ala Arg Arg Met Ile Glu Gly Val Ala Tyr Glu Met Arg Val Tyr
    1370            1375                1380

Ala Val Asn Ala Val Gly Met Ser Arg Pro Ser Pro Ala Ser Gln
    1385            1390                1395

Pro Phe Met Pro Ile Gly Pro Pro Gly Glu Pro Thr His Leu Ala
    1400            1405                1410

Val Glu Asp Val Ser Asp Thr Thr Val Ser Leu Lys Trp Arg Pro
    1415            1420                1425

Pro Glu Arg Val Gly Ala Gly Gly Leu Asp Gly Tyr Ser Val Glu
    1430            1435                1440

Tyr Cys Gln Glu Gly Cys Ser Glu Trp Thr Pro Ala Leu Gln Gly
    1445            1450                1455

Leu Thr Glu Arg Thr Ser Met Leu Val Lys Asp Leu Pro Thr Gly
    1460            1465                1470

Ala Arg Leu Leu Phe Arg Val Arg Ala His Asn Val Ala Gly Pro
    1475            1480                1485

Gly Gly Pro Ile Val Thr Lys Glu Pro Val Thr Val Gln Glu Ile
    1490            1495                1500

Leu Gln Arg Pro Arg Leu Gln Leu Pro Arg His Leu Arg Gln Thr
    1505            1510                1515

Ile Gln Lys Lys Val Gly Glu Pro Val Asn Leu Leu Ile Pro Phe
    1520            1525                1530
```

```
Gln Gly Lys Pro Arg Pro Gln Val Thr Trp Thr Lys Glu Gly Gln
    1535                1540                1545

Pro Leu Ala Gly Glu Glu Val Ser Ile Arg Asn Ser Pro Thr Asp
    1550                1555                1560

Thr Ile Leu Phe Ile Arg Ala Ala Arg Arg Thr His Ser Gly Thr
    1565                1570                1575

Tyr Gln Val Thr Val Arg Ile Glu Asn Met Glu Asp Lys Ala Thr
    1580                1585                1590

Leu Ile Leu Gln Ile Val Asp Lys Pro Ser Pro Gln Asp Ile
    1595                1600                1605

Arg Ile Val Glu Thr Trp Gly Phe Asn Val Ala Leu Glu Trp Lys
    1610                1615                1620

Pro Pro Gln Asp Asp Gly Asn Thr Glu Ile Trp Gly Tyr Thr Val
    1625                1630                1635

Gln Lys Ala Asp Lys Lys Thr Met Glu Trp Phe Thr Val Leu Glu
    1640                1645                1650

His Tyr Arg Arg Thr His Cys Val Val Ser Glu Leu Ile Ile Gly
    1655                1660                1665

Asn Gly Tyr Tyr Phe Arg Val Phe Ser His Asn Met Val Gly Ser
    1670                1675                1680

Ser Asp Lys Ala Ala Ala Thr Lys Glu Pro Val Phe Ile Pro Arg
    1685                1690                1695

Pro Gly Ile Thr Tyr Glu Pro Pro Lys Tyr Lys Ala Leu Asp Phe
    1700                1705                1710

Ser Glu Ala Pro Ser Phe Thr Gln Pro Leu Ala Asn Arg Ser Ile
    1715                1720                1725

Ile Ala Gly Tyr Asn Ala Ile Leu Cys Cys Ala Val Arg Gly Ser
    1730                1735                1740

Pro Lys Pro Lys Ile Ser Trp Phe Lys Asn Gly Leu Asp Leu Gly
    1745                1750                1755

Glu Asp Ala Arg Phe Arg Met Phe Cys Lys Gln Gly Val Leu Thr
    1760                1765                1770

Leu Glu Ile Arg Lys Pro Cys Pro Tyr Asp Gly Gly Val Tyr Val
    1775                1780                1785

Cys Arg Ala Thr Asn Leu Gln Gly Glu Ala Gln Cys Glu Cys Arg
    1790                1795                1800

Leu Glu Val Arg Val Pro Gln
    1805                1810

<210> SEQ ID NO 2
<211> LENGTH: 1274
<212> TYPE: PRT
<213> ORGANISM: Homo sapiens

<400> SEQUENCE: 2

Met Pro Glu Pro Gly Lys Lys Pro Val Ser Ala Phe Ser Lys Pro
1               5                   10                  15

Arg Ser Val Glu Val Ala Ala Gly Ser Pro Ala Val Phe Glu Ala
                20                  25                  30

Thr Glu Arg Ala Gly Val Lys Val Arg Trp Gln Arg Gly Gly Ser Asp
            35                  40                  45

Ile Ser Ala Ser Asn Lys Tyr Gly Leu Ala Thr Glu Gly Thr Arg His
        50                  55                  60

Thr Leu Thr Val Arg Glu Val Gly Pro Ala Asp Gln Gly Ser Tyr Ala
65                  70                  75                  80
```

```
Val Ile Ala Gly Ser Ser Lys Val Lys Phe Asp Leu Lys Val Ile Glu
                85                  90                  95
Ala Glu Lys Ala Glu Pro Met Leu Ala Pro Ala Pro Ala Pro Ala Glu
                100                 105                 110
Ala Thr Gly Ala Pro Gly Glu Ala Pro Ala Pro Ala Ala Glu Leu Gly
                115                 120                 125
Glu Ser Ala Pro Ser Pro Lys Gly Ser Ser Ala Ala Leu Asn Gly
    130                 135                 140
Pro Thr Pro Gly Ala Pro Asp Asp Pro Ile Gly Leu Phe Val Met Arg
145                 150                 155                 160
Pro Gln Asp Gly Glu Val Thr Val Gly Gly Ser Ile Thr Phe Ser Ala
                165                 170                 175
Arg Val Ala Gly Ala Ser Leu Leu Lys Pro Pro Val Val Lys Trp Phe
                180                 185                 190
Lys Gly Lys Trp Val Asp Leu Ser Ser Lys Val Gly Gln His Leu Gln
                195                 200                 205
Leu His Asp Ser Tyr Asp Arg Ala Ser Lys Val Tyr Leu Phe Glu Leu
    210                 215                 220
His Ile Thr Asp Ala Gln Pro Ala Phe Thr Gly Ser Tyr Arg Cys Glu
225                 230                 235                 240
Val Ser Thr Lys Asp Lys Phe Asp Cys Ser Asn Phe Asn Leu Thr Val
                245                 250                 255
His Glu Ala Met Gly Thr Gly Asp Leu Asp Leu Leu Ser Ala Phe Arg
                260                 265                 270
Arg Thr Ser Leu Ala Gly Gly Arg Arg Ile Ser Asp Ser His Glu
    275                 280                 285
Asp Thr Gly Ile Leu Asp Phe Ser Ser Leu Leu Lys Lys Arg Asp Ser
    290                 295                 300
Phe Arg Thr Pro Arg Asp Ser Lys Leu Glu Ala Pro Ala Glu Glu Asp
305                 310                 315                 320
Val Trp Glu Ile Leu Arg Gln Ala Pro Pro Ser Glu Tyr Glu Arg Ile
                325                 330                 335
Ala Phe Gln Tyr Gly Val Thr Asp Leu Arg Gly Met Leu Lys Arg Leu
                340                 345                 350
Lys Gly Met Arg Arg Asp Glu Lys Lys Ser Thr Ala Phe Gln Lys Lys
                355                 360                 365
Leu Glu Pro Ala Tyr Gln Val Ser Lys Gly His Lys Ile Arg Leu Thr
    370                 375                 380
Val Glu Leu Ala Asp His Asp Ala Glu Val Lys Trp Leu Lys Asn Gly
385                 390                 395                 400
Gln Glu Ile Gln Met Ser Gly Ser Lys Tyr Ile Phe Glu Ser Ile Gly
                405                 410                 415
Ala Lys Arg Thr Leu Thr Ile Ser Gln Cys Ser Leu Ala Asp Asp Ala
                420                 425                 430
Ala Tyr Gln Cys Val Val Gly Gly Glu Lys Cys Ser Thr Glu Leu Phe
                435                 440                 445
Val Lys Glu Pro Pro Val Leu Ile Thr Arg Pro Leu Glu Asp Gln Leu
    450                 455                 460
Val Met Val Gly Gln Arg Val Glu Phe Glu Cys Glu Val Ser Glu Glu
465                 470                 475                 480
Gly Ala Gln Val Lys Trp Leu Lys Asp Gly Val Glu Leu Thr Arg Glu
                485                 490                 495
```

```
Glu Thr Phe Lys Tyr Arg Phe Lys Lys Asp Gly Gln Arg His His Leu
                500                 505                 510

Ile Ile Asn Glu Ala Met Leu Glu Asp Ala Gly His Tyr Ala Leu Cys
            515                 520                 525

Thr Ser Gly Gly Gln Ala Leu Ala Glu Leu Ile Val Gln Glu Lys Lys
        530                 535                 540

Leu Glu Val Tyr Gln Ser Ile Ala Asp Leu Met Val Gly Ala Lys Asp
545                 550                 555                 560

Gln Ala Val Phe Lys Cys Glu Val Ser Asp Glu Asn Val Arg Gly Val
                565                 570                 575

Trp Leu Lys Asn Gly Lys Glu Leu Val Pro Asp Ser Arg Ile Lys Val
            580                 585                 590

Ser His Ile Gly Arg Val His Lys Leu Thr Ile Asp Asp Val Thr Pro
        595                 600                 605

Ala Asp Glu Ala Asp Tyr Ser Phe Val Pro Glu Gly Phe Ala Cys Asn
610                 615                 620

Leu Ser Ala Lys Leu His Phe Met Glu Val Lys Ile Asp Phe Val Pro
625                 630                 635                 640

Arg Gln Glu Pro Pro Lys Ile His Leu Asp Cys Pro Gly Arg Ile Pro
                645                 650                 655

Asp Thr Ile Val Val Val Ala Gly Asn Lys Leu Arg Leu Asp Val Pro
            660                 665                 670

Ile Ser Gly Asp Pro Ala Pro Thr Val Ile Trp Gln Lys Ala Ile Thr
        675                 680                 685

Gln Gly Asn Lys Ala Pro Ala Arg Pro Ala Pro Asp Ala Pro Glu Asp
690                 695                 700

Thr Gly Asp Ser Asp Glu Trp Val Phe Asp Lys Lys Leu Leu Cys Glu
705                 710                 715                 720

Thr Glu Gly Arg Val Arg Val Glu Thr Thr Lys Asp Arg Ser Ile Phe
                725                 730                 735

Thr Val Glu Gly Ala Glu Lys Glu Asp Glu Gly Val Tyr Thr Val Thr
            740                 745                 750

Val Lys Asn Pro Val Gly Glu Asp Gln Val Asn Leu Thr Val Lys Val
        755                 760                 765

Ile Asp Val Pro Asp Ala Pro Ala Ala Pro Lys Ile Ser Asn Val Gly
770                 775                 780

Glu Asp Ser Cys Thr Val Gln Trp Glu Pro Pro Ala Tyr Asp Gly Gly
785                 790                 795                 800

Gln Pro Ile Leu Gly Tyr Ile Leu Glu Arg Lys Lys Lys Lys Ser Tyr
                805                 810                 815

Arg Trp Met Arg Leu Asn Phe Asp Leu Ile Gln Glu Leu Ser His Glu
            820                 825                 830

Ala Arg Arg Met Ile Glu Gly Val Val Tyr Glu Met Arg Val Tyr Ala
        835                 840                 845

Val Asn Ala Ile Gly Met Ser Arg Pro Ser Pro Ala Ser Gln Pro Phe
850                 855                 860

Met Pro Ile Gly Pro Pro Ser Glu Pro Thr His Leu Ala Val Glu Asp
865                 870                 875                 880

Val Ser Asp Thr Thr Val Ser Leu Lys Trp Arg Pro Pro Glu Arg Val
                885                 890                 895

Gly Ala Gly Gly Leu Asp Gly Tyr Ser Val Glu Tyr Cys Pro Glu Gly
            900                 905                 910

Cys Ser Glu Trp Val Ala Ala Leu Gln Gly Leu Thr Glu His Thr Ser
```

```
            915                 920                 925
Ile Leu Val Lys Asp Leu Pro Thr Gly Ala Arg Leu Leu Phe Arg Val
        930                 935                 940
Arg Ala His Asn Met Ala Gly Pro Gly Ala Pro Val Thr Thr Thr Glu
945                 950                 955                 960
Pro Val Thr Val Gln Glu Ile Leu Gln Arg Pro Arg Leu Gln Leu Pro
                965                 970                 975
Arg His Leu Arg Gln Thr Ile Gln Lys Lys Val Gly Glu Pro Val Asn
            980                 985                 990
Leu Leu Ile Pro Phe Gln Gly Lys Pro Arg Pro Gln Val Thr Trp Thr
            995                 1000                1005
Lys Glu Gly Gln Pro Leu Ala Gly Glu Val Ser Ile Arg Asn
    1010                1015                1020
Ser Pro Thr Asp Thr Ile Leu Phe Ile Arg Ala Ala Arg Arg Val
    1025                1030                1035
His Ser Gly Thr Tyr Gln Val Thr Val Arg Ile Glu Asn Met Glu
    1040                1045                1050
Asp Lys Ala Thr Leu Val Leu Gln Val Val Asp Lys Pro Ser Pro
    1055                1060                1065
Pro Gln Asp Leu Arg Val Thr Asp Ala Trp Gly Leu Asn Val Ala
    1070                1075                1080
Leu Glu Trp Lys Pro Pro Gln Asp Val Gly Asn Thr Glu Leu Trp
    1085                1090                1095
Gly Tyr Thr Val Gln Lys Ala Asp Lys Lys Thr Met Glu Trp Phe
    1100                1105                1110
Thr Val Leu Glu His Tyr Arg Arg Thr His Cys Val Val Pro Glu
    1115                1120                1125
Leu Ile Ile Gly Asn Gly Tyr Tyr Phe Arg Val Phe Ser Gln Asn
    1130                1135                1140
Met Val Gly Phe Ser Asp Arg Ala Ala Thr Thr Lys Glu Pro Val
    1145                1150                1155
Phe Ile Pro Arg Pro Gly Ile Thr Tyr Glu Pro Pro Asn Tyr Lys
    1160                1165                1170
Ala Leu Asp Phe Ser Glu Ala Pro Ser Phe Thr Gln Pro Leu Val
    1175                1180                1185
Asn Arg Ser Val Ile Ala Gly Tyr Thr Ala Met Leu Cys Cys Ala
    1190                1195                1200
Val Arg Gly Ser Pro Lys Pro Lys Ile Ser Trp Phe Lys Asn Gly
    1205                1210                1215
Leu Asp Leu Gly Glu Asp Ala Arg Phe Arg Met Phe Ser Lys Gln
    1220                1225                1230
Gly Val Leu Thr Leu Glu Ile Arg Lys Pro Cys Pro Phe Asp Gly
    1235                1240                1245
Gly Ile Tyr Val Cys Arg Ala Thr Asn Leu Gln Gly Glu Ala Arg
    1250                1255                1260
Cys Glu Cys Arg Leu Glu Val Arg Val Pro Gln
    1265                1270

<210> SEQ ID NO 3
<211> LENGTH: 3813
<212> TYPE: DNA
<213> ORGANISM: Mus musculus

<400> SEQUENCE: 3
```

```
atgccggagc cagggaagaa accagtgtca gccttcaaca agaagccaag gtcagcggag    60
gtgaccgctg gcagtgctgc cgtgttcgag gctgggacgg agcggtcagg cgtgaaggtg   120
cggtggcagc gggatggcag cgacatcacc gccaatgaca agtatggttt ggcagcagag   180
ggcaagcgac acacactgac agtgcgggat gcgagccctg atgaccaggg ttcctacgcg   240
gtcattgcag gctcctcaaa ggtcaagttt gacctcaagg tcacagagcc agcccctcca   300
gagaaggcag aatctgaagt tgctccagga gcccccaaag aagtccctgc tccagccact   360
gagttggaag aaagtgtctc aagtcctgaa gggtcagtct cggtaaccca ggatggctca   420
gctgcagagc atcagggagc ccctgatgac cctattggcc tctttctgat gcgaccacag   480
gatggtgagg tgaccgtggg cggcagcatt gtcttctcag cccgagtggc tggggccagc   540
ctcctgaaac cgcctgtggt caagtggttc aagggcaagt gggtggacct gagcagcaaa   600
gtgggccagc acctgcagct gcatgacagc tatgacagag ccagcaaggt ctacttgttt   660
gagttgcaca tcacagatgc tcagaccact tctgctgggg gctaccgctg tgaggtgtct   720
accaaggaca aatttgacag ctgtagcttc aacctcactg tccatgaggc cattggttct   780
ggagacctgg acctcagatc agcttttcga cgcacgagcc tggcgggagc aggtcggaga   840
accagtgaca gccatgaaga tgctgggact ctggacttta gttccctgct gaagaagaga   900
gacagtttcc ggagggactc aaagctggag gcacctgctg aagaagacgt gtgggagatc   960
ctgagacagg caccgccgtc agaatatgag cgcatcgcct tccagcacgg agtcacagac  1020
cttcgaggca tgctgaagag gctcaagggc atgaagcagg atgaaaagaa gagcacagcc  1080
tttcagaaga gctggagcc tgcctaccag gtaaacaagg ccacaagat tcggcttact  1140
gtggaactgg ctgatccgga cgccgaagtc aagtggctta agaatggaca ggagatccag  1200
atgagtggca gcaagtacat cttcgagtcc gtcggtgcca agcgcaccct gaccatcagc  1260
cagtgctcac tggctgacga cgcagcctac cagtgtgtgg tgggggcga aagtgcagc  1320
acggagctct ttgtcaaaga gccccggtg ctgatcactc ggtccctgga agaccagctg  1380
gtgatggtgg gtcagcgggt ggagtttgag tgtgaggtct cagaagaagg ggcccaagtc  1440
aaatggctga aggatggggt tgaactgaca cgtgaggaga ccttcaaata ccggttcaag  1500
aaagatgggc ggaaacacca cttgatcatc aatgaagcaa ccctggagga tgcaggacac  1560
tatgcagtac gcacaagtgg aggccagtca ctggctgagc tcattgtgca agagaagaag  1620
ttggaggtat accaaagcat cgcggacctg gcagtgggag ccaaggacca ggctgtgttt  1680
aagtgtgagg tttcagatga gaatgtacgc ggcgtgtggc tgaagaatgg aaggaactg  1740
gtgcctgaca accgcataaa ggtgtcccat ataggccggg tccacaaact gaccattgac  1800
gatgtcacac tgctgatga ggctgactac agctttgtcc ctgaagggtt tgcctgcaac  1860
ctgtctgcca agctccactt catggaggtc aagattgact ttgtgcctag gcaggaacct  1920
cccaagatcc acttggattg tcccggcagc acaccagaca ccattgtggt tgttgctggg  1980
aacaagttac gcctggatgt ccctatttct ggagaccctg ctcccactgt ggtctggcag  2040
aagactgtaa cacaggggaa gaaggcctca actgggccac accctgatgc cccagaagat  2100
gctggtgctg atgaggagtg ggtgtttgat aagaagctgt tgtgtgagac tgagggccgg  2160
gtccgggtgg agaccaccaa agaccgcagc gtctttacag tcgaaggggc agggaaggaa  2220
gatgaaggtg tctacacagt cacagtaaag aaccccgtgg gcgaggacca ggtcaacctc  2280
acagtcaagg tcatcgatgt cccagatgct cctgcggccc ctaagatcag caacgtgggc  2340
gaggactcct gcactgtgca gtgggaaccg cctgcctatg atggcgggca gccggtcctg  2400
```

```
ggatacatcc tggagcgcaa gaagaaaaag agctacaggt ggatgaggct caactttgat    2460
ctgctgcggg agctgagcca cgaggcgagg cgcatgatcg agggtgtagc ctatgagatg    2520
cgagtctacg cagtcaatgc cgtgggaatg tccaggccca gccctgcctc tcagcccttc    2580
atgcctattg ggcccctgg cgaaccaacc cacttggctg tggaggatgt gtcagacacc    2640
actgtctcac tcaagtggcg gcccccagag cgcgtggggg ccggtggcct ggacggatac    2700
agcgtggagt actgccagga gggatgctcc gagtggacac ctgctctgca ggggctgaca    2760
gagcgcacat cgatgctggt gaaggaccta cccactgggg cacggctgct gttccgagta    2820
cgggcacaca atgtggcagg tcctggaggc cctatcgtca ccaaggagcc tgtgacagtg    2880
caggagatac tgcaacgacc acggctccaa ctgcccagac acctgcgcca gaccatccag    2940
aagaaagttg gggagcctgt gaacctcctc atcccttttcc agggcaaacc ccggcctcag    3000
gtgacctgga ccaaagaggg gcagcccctg gcaggtgagg aggtgagcat ccggaacagc    3060
cccacagaca cgatcttgtt catccgagct gcccgccgca cccactcggg cacctaccag    3120
gtgacagttc gcattgagaa catggaggac aaggcaacgc tgatcctgca gattgtggac    3180
aagccaagtc ctccccagga tatccggatc gttgagactt ggggtttcaa gtgggctctg    3240
gagtggaagc accccaaga tgatggcaat acagagatct ggggttatac tgtacagaaa    3300
gctgacaaga agaccatgga gtggttcacg gttttggaac actaccgacg cactcactgt    3360
gtggtatcag agcttatcat tggcaatggc tactacttcc gggtcttcag ccataacatg    3420
gtgggttcca gtgacaaagc tgccgccacc aaggagccag tctttattcc aagaccaggc    3480
atcacatatg agccacccaa atacaaggcc ctggacttct ctgaggcccc aagcttcacc    3540
cagcccttgg caaatcgctc catcattgca ggctataatg ccatcctctg ctgtgctgtc    3600
cgaggtagtc ctaagcccaa gatttcctgg ttcaagaatg gcctggatct gggagaagat    3660
gctcgcttcc gcatgttctg caagcaggga gtattgaccc tggagatcag gaaaccctgc    3720
ccctatgatg gtggtgtcta tgtctgcagg gccaccaact gcagggcga ggcacagtgt    3780
gagtgccgcc tggaggtgcg agttcctcag tga                                 3813
```

<210> SEQ ID NO 4
<211> LENGTH: 4217
<212> TYPE: DNA
<213> ORGANISM: Homo sapiens

<400> SEQUENCE: 4

```
agtccctctt tgggtgacct gtgcctgctt cgtgcctggt gtgacgtctc tcaggatgcc      60
tgagccgggg aagaagccag tctcagcttt tagcaagaag ccacggtcag tggaagtggc     120
cgcaggcagc cctgccgtgt cgaggccga cagagcgg gcaggagtga aggtgcgctg        180
gcagcgcgga ggcagtgaca tcagcgccag caacaagtac ggcctggcca cagagggcac     240
acggcatacg ctgacagtgc gggaagtggg ccctgccgac cagggatctt acgcagtcat     300
tgctggctcc tccaaggtca agttcgacct caaggtcata gaggcagaga aggcagagcc     360
catgctggcc cctgccctg cccctgctga ggccactgga gccctggag aagcccggc         420
cccagccgct gagctgggag aaagtgcccc aagtcccaaa gggtcaagct cagcagctct     480
caatggtcct acccctggag ccccgatga cccattggc ctcttcgtga tgcggccaca        540
ggatggcgag gtgaccgtgg gtggcagcat caccttctca gcccgcgtgg ccggcgccag     600
cctcctgaag ccgcctgtgg tcaagtggtt caagggcaaa tgggtggacc tgagcagcaa     660
```

```
ggtgggccag cacctgcagc tgcacgacag ctacgaccgc gccagcaagg tctatctgtt    720
cgagctgcac atcaccgatg cccagcctgc cttcactggc agctaccgct gtgaggtgtc    780
caccaaggac aaatttgact gctccaactt caatctcact gtccacgagg ccatgggcac    840
cggagacctg gacctcctat cagccttccg ccgcacgagc ctggctggag gtggtcggcg    900
gatcagtgat agccatgagg acactgggat tctggacttc agctcactgc tgaaaaagag    960
agacagtttc cggaccccga gggactcgaa gctggaggca ccagcagagg aggacgtgtg   1020
ggagatccta cggcaggcac ccccatctga gtacgagcgc atcgccttcc agtacggcgt   1080
cactgacctg cgcggcatgc taaagaggct caagggcatg aggcgcgatg agaagaagag   1140
cacagccttt cagaagaagc tggagccggc ctaccaggtg agcaaaggcc acaagatccg   1200
gctgaccgtg gaactggctg accatgacgc tgaggtcaaa tggctcaaga atggccagga   1260
gatccagatg agcggcagca agtacatctt tgagtccatc ggtgccaagc gtaccctgac   1320
catcagccag tgctcattgg cggacgacgc agcctaccag tgcgtggtgg gtggcgagaa   1380
gtgtagcacg gagctctttg tgaaagagcc ccctgtgctc atcacgcgcc ccttggagga   1440
ccagctggtg atggtggggc agcgggtgga gtttgagtgt gaagtatcgg aggaggggc    1500 gcaagtcaaa tggctgaagg acggggtgga gctgacccgg gaggagacct tcaaataccg   1560
gttcaagaag gacgggcaga gacaccacct gatcatcaac gaggccatgc tggaggacgc   1620
ggggcactat gcactgtgca ctagcggggg ccaggcgctg gctgagctca ttgtgcagga   1680
aaagaagctg gaggtgtacc agagcatcgc agacctgatg gtgggcgcaa aggaccaggc   1740
ggtgttcaaa tgtgaggtct cagatgagaa tgttcgggt gtgtggctga agaatgggaa    1800
ggagctggtg cccgacagcc gcataaaggt gtcccacatc gggcgggtcc acaaactgac   1860
cattgacgac gtcacacctg ccgacgaggc tgactacagc tttgtgcccg agggcttcgc   1920
ctgcaacctg tcagccaagc tccacttcat ggaggtcaag attgacttcg tacccaggca   1980
ggaacctccc aagatccacc tggactgccc aggccgcata ccagacacca ttgtggttgt   2040
agctggaaat aagctacgtc tggacgtccc tatctctggg gaccctgctc ccactgtgat   2100
ctggcagaag gctatcacgc aggggaataa ggccccagcc aggccagccc cagatgcccc   2160
agaggacaca ggtgacagcg atgagtgggt gtttgacaag aagctgctgt gtgagaccga   2220
gggccgggtc cgcgtggaga ccaccaagga ccgcagcatc ttcacggtcg aggggggcaga   2280 gaaggaagat gagggcgtct acacggtcac agtgaagaac cctgtgggcg aggaccaggt   2340
caacctcaca gtcaaggtca tcgacgtgcc agacgcacct gcggcccccca agatcagcaa   2400 cgtgggagag gactcctgca cagtacagtg ggagccgcct gcctacgatg gcgggcagcc   2460
catcctgggc tacatcctgg agcgcaagaa gaagaagagc taccggtgga tgcggctgaa   2520
cttcgacctg attcaggagc tgagtcatga acgcggcgc atgatcgagg gcgtggtgta    2580
cgagatgcgc gtctacgcgg tcaacgccat cggcatgtcc aggcccagcc ctgcctccca   2640
gcccttcatg cctatcggtc cccccagcga acccacccac ctggcagtag aggacgtctc   2700
tgacaccacg gtctccctca gtggcggcc cccagagcgc gtgggagcag gaggcctgga   2760
tggctacagc gtggagtact gcccagaggg ctgctcagag tgggtggctg ccctgcaggg   2820
gctgacagag cacacatcga tactggtgaa ggacctgccc acgggggccc ggctgctttt   2880
ccgagtgcgg gcacacaata tggcagggc tggagcccct gttaccacca cggagccggt    2940
gacagtgcag gagatcctgc aacgccacg gcttcagctg cccaggcacc tgcgccagac   3000
cattcagaag aaggtcgggg agcctgtgaa ccttctcatc cctttccagg gcaagccccg   3060
```

```
gcctcaggtg acctggacca aagaggggca gccccctggca ggcgaggagg tgagcatccg    3120
caacagcccc acagacacca tcctgttcat ccgggccgct cgccgcgtgc attcaggcac    3180
ttaccaggtg acggtgcgca ttgagaacat ggaggacaag gccacgctgg tgctgcaggt    3240
tgttgacaag ccaagtcctc cccaggatct ccgggtgact gacgcctggg gtcttaatgt    3300
ggctctggag tggaagccac cccaggatgt cggcaacacg gagctctggg ggtacacagt    3360
gcagaaagcc gacaagaaga ccatggagtg gttcaccgtc ttggagcatt accgccgcac    3420
ccactgcgtg gtgccagagc tcatcattgg caatggctac tacttccgcg tcttcagcca    3480
gaatatggtt ggctttagtg acagagcggc caccaccaag gagcccgtct ttatccccag    3540
accaggcatc acctatgagc acccaactaa taaggccctg gacttctccg aggccccaag    3600
cttcacccag cccctggtga accgctcggt catcgcgggc tacactgcta tgctctgctg    3660
tgctgtccgg ggtagcccca agcccaagat ttcctggttc aagaatggcc tggacctggg    3720
agaagacgcc cgcttccgca tgttcagcaa gcagggagtg ttgactctgg agattagaaa    3780
gccctgcccc tttgacgggg gcatctatgt ctgcagggcc accaacttac agggcgaggc    3840
acggtgtgag tgccgcctgg aggtgcgagt gcctcagtga ccaggctggc tcctggggat    3900
ggccaggtac aaccggatgc cagccccgtg ccaggagcct ggagggaagt tggggaaacc    3960
cctccctact gttggatgta tgtgtgacaa gtgtgtctcc tgtgctgcga tgggggatca    4020
gcagggcagt tgtcgggcag tcctgagtgg gtgttgcaca gactggtcca cagggctcct    4080
gaaggaagcc cctggatctt tggggtaaaa ggagggtggc ctcaagaaac aatgtctggg    4140
gacaggcctt tctggcctgc tatgtcttcc caatgtttat tgggcaataa aagataagtg    4200
cagtcacaga gaactca                                                   4217

<210> SEQ ID NO 5
<211> LENGTH: 1270
<212> TYPE: PRT
<213> ORGANISM: Mus musculus

<400> SEQUENCE: 5

Met Pro Glu Pro Gly Lys Lys Pro Val Ser Ala Phe Asn Lys Lys Pro
1               5                   10                  15

Arg Ser Ala Glu Val Thr Ala Gly Ser Ala Ala Val Phe Glu Ala Gly
            20                  25                  30

Thr Glu Arg Ser Gly Val Lys Val Arg Trp Gln Arg Asp Gly Ser Asp
        35                  40                  45

Ile Thr Ala Asn Asp Lys Tyr Gly Leu Ala Ala Glu Gly Lys Arg His
    50                  55                  60

Thr Leu Thr Val Arg Asp Ala Ser Pro Asp Asp Gln Gly Ser Tyr Ala
65                  70                  75                  80

Val Ile Ala Gly Ser Ser Lys Val Lys Phe Asp Leu Lys Val Thr Glu
                85                  90                  95

Pro Ala Pro Pro Glu Lys Ala Glu Ser Glu Val Ala Pro Gly Ala Pro
            100                 105                 110

Lys Glu Val Pro Ala Pro Ala Thr Glu Leu Glu Glu Ser Val Ser Ser
        115                 120                 125

Pro Glu Gly Ser Val Ser Val Thr Gln Asp Gly Ser Ala Ala Glu His
    130                 135                 140

Gln Gly Ala Pro Asp Asp Pro Ile Gly Leu Phe Leu Met Arg Pro Gln
145                 150                 155                 160
```

-continued

```
Asp Gly Glu Val Thr Val Gly Gly Ser Ile Val Phe Ser Ala Arg Val
            165                 170                 175
Ala Gly Ala Ser Leu Leu Lys Pro Pro Val Val Lys Trp Phe Lys Gly
            180                 185                 190
Lys Trp Val Asp Leu Ser Ser Lys Val Gly Gln His Leu Gln Leu His
            195                 200                 205
Asp Ser Tyr Asp Arg Ala Ser Lys Val Tyr Leu Phe Glu Leu His Ile
            210                 215                 220
Thr Asp Ala Gln Thr Thr Ser Ala Gly Gly Tyr Arg Cys Glu Val Ser
225                 230                 235                 240
Thr Lys Asp Lys Phe Asp Ser Cys Ser Phe Asn Leu Thr Val His Glu
                245                 250                 255
Ala Ile Gly Ser Gly Asp Leu Asp Leu Arg Ser Ala Phe Arg Arg Thr
            260                 265                 270
Asp Leu Ala Gly Ala Gly Arg Arg Thr Asp Asp Ser His Glu Asp Ala
            275                 280                 285
Gly Thr Leu Asp Phe Ser Ser Leu Leu Lys Lys Arg Asp Asp Phe Arg
            290                 295                 300
Arg Asp Ser Lys Leu Glu Ala Pro Ala Glu Glu Asp Val Trp Glu Ile
305                 310                 315                 320
Leu Arg Gln Ala Pro Pro Ser Glu Tyr Glu Arg Ile Ala Phe Gln His
                325                 330                 335
Gly Val Thr Asp Leu Arg Gly Met Leu Lys Arg Leu Lys Gly Met Lys
            340                 345                 350
Gln Asp Glu Lys Lys Ser Thr Ala Phe Gln Lys Lys Leu Glu Pro Ala
            355                 360                 365
Tyr Gln Val Asn Lys Gly His Lys Ile Arg Leu Thr Val Glu Leu Ala
            370                 375                 380
Asp Pro Asp Ala Glu Val Lys Trp Leu Lys Asn Gly Gln Glu Ile Gln
385                 390                 395                 400
Met Ser Gly Ser Lys Tyr Ile Phe Glu Ser Val Gly Ala Lys Arg Thr
                405                 410                 415
Leu Thr Ile Ser Gln Cys Ser Leu Ala Asp Asp Ala Ala Tyr Gln Cys
            420                 425                 430
Val Val Gly Gly Glu Lys Cys Ser Thr Glu Leu Phe Val Lys Glu Pro
            435                 440                 445
Pro Val Leu Ile Thr Arg Ser Leu Glu Asp Gln Leu Val Met Val Gly
            450                 455                 460
Gln Arg Val Glu Phe Glu Cys Glu Val Ser Glu Glu Gly Ala Gln Val
465                 470                 475                 480
Lys Trp Leu Lys Asp Gly Val Glu Leu Thr Arg Glu Glu Thr Phe Lys
                485                 490                 495
Tyr Arg Phe Lys Lys Asp Gly Arg Lys His His Leu Ile Ile Asn Glu
            500                 505                 510
Ala Thr Leu Glu Asp Ala Gly His Tyr Ala Val Arg Thr Ser Gly Gly
            515                 520                 525
Gln Ser Leu Ala Glu Leu Ile Val Gln Glu Lys Lys Leu Glu Val Tyr
            530                 535                 540
Gln Ser Ile Ala Asp Leu Ala Val Gly Ala Lys Asp Gln Ala Val Phe
545                 550                 555                 560
Lys Cys Glu Val Ser Asp Glu Asn Val Arg Gly Val Trp Leu Lys Asn
                565                 570                 575
Gly Lys Glu Leu Val Pro Asp Asn Arg Ile Lys Val Ser His Ile Gly
```

-continued

```
                580                 585                 590
Arg Val His Lys Leu Thr Ile Asp Asp Val Thr Pro Ala Asp Glu Ala
            595                 600                 605
Asp Tyr Ser Phe Val Pro Glu Gly Phe Ala Cys Asn Leu Ser Ala Lys
        610                 615                 620
Leu His Phe Met Glu Val Lys Ile Asp Phe Val Pro Arg Gln Glu Pro
625                 630                 635                 640
Pro Lys Ile His Leu Asp Cys Pro Gly Ser Thr Pro Asp Thr Ile Val
                645                 650                 655
Val Val Ala Gly Asn Lys Leu Arg Leu Asp Val Pro Ile Ser Gly Asp
            660                 665                 670
Pro Ala Pro Thr Val Val Trp Gln Lys Thr Val Thr Gln Gly Lys Lys
        675                 680                 685
Ala Ser Thr Gly Pro His Pro Asp Ala Pro Glu Asp Ala Gly Ala Asp
        690                 695                 700
Glu Glu Trp Val Phe Asp Lys Lys Leu Leu Cys Glu Thr Gly Arg
705                 710                 715                 720
Val Arg Val Glu Thr Thr Lys Asp Arg Ser Val Phe Thr Val Glu Gly
                725                 730                 735
Ala Gly Lys Glu Asp Glu Gly Val Tyr Thr Val Thr Val Lys Asn Pro
            740                 745                 750
Val Gly Glu Asp Gln Val Asn Leu Thr Val Lys Val Ile Asp Val Pro
        755                 760                 765
Asp Ala Pro Ala Ala Pro Lys Ile Ser Asn Val Gly Glu Asp Ser Cys
        770                 775                 780
Thr Val Gln Trp Glu Pro Pro Ala Tyr Asp Gly Gly Gln Pro Val Leu
785                 790                 795                 800
Gly Tyr Ile Leu Glu Arg Lys Lys Lys Ser Tyr Arg Trp Met Arg
                805                 810                 815
Leu Asn Phe Asp Leu Leu Arg Glu Leu Ser His Glu Ala Arg Arg Met
            820                 825                 830
Ile Glu Gly Val Ala Tyr Glu Met Arg Val Tyr Ala Val Asn Ala Val
        835                 840                 845
Gly Met Ser Arg Pro Ser Pro Ala Ser Gln Pro Phe Met Pro Ile Gly
        850                 855                 860
Pro Pro Gly Glu Pro Thr His Leu Ala Val Glu Asp Val Ser Asp Thr
865                 870                 875                 880
Thr Val Ser Leu Lys Trp Arg Pro Pro Glu Arg Val Gly Ala Gly Gly
                885                 890                 895
Leu Asp Gly Tyr Ser Val Glu Tyr Cys Gln Glu Gly Cys Ser Glu Trp
            900                 905                 910
Thr Pro Ala Leu Gln Gly Leu Thr Glu Arg Thr Ser Met Leu Val Lys
        915                 920                 925
Asp Leu Pro Thr Gly Ala Arg Leu Leu Phe Arg Val Arg Ala His Asn
        930                 935                 940
Val Ala Gly Pro Gly Gly Pro Ile Val Thr Lys Glu Pro Val Thr Val
945                 950                 955                 960
Gln Glu Ile Leu Gln Arg Pro Arg Leu Gln Leu Pro Arg His Leu Arg
                965                 970                 975
Gln Thr Ile Gln Lys Lys Val Gly Glu Pro Val Asn Leu Leu Ile Pro
            980                 985                 990
Phe Gln Gly Lys Pro Arg Pro Gln  Val Thr Trp Thr Lys  Glu Gly Gln
            995                1000                1005
```

```
Pro Leu Ala Gly Glu Glu Val Ser Ile Arg Asn Ser Pro Thr Asp
    1010                1015                1020

Thr Ile Leu Phe Ile Arg Ala Ala Arg Thr His Ser Gly Thr
    1025                1030                1035

Tyr Gln Val Thr Val Arg Ile Glu Asn Met Glu Asp Lys Ala Thr
    1040                1045                1050

Leu Ile Leu Gln Ile Val Asp Lys Pro Ser Pro Gln Asp Ile
    1055                1060                1065

Arg Ile Val Glu Thr Trp Gly Phe Asn Val Ala Leu Glu Trp Lys
    1070                1075                1080

Pro Pro Gln Asp Asp Gly Asn Thr Glu Ile Trp Gly Tyr Thr Val
    1085                1090                1095

Gln Lys Ala Asp Lys Lys Thr Met Glu Trp Phe Thr Val Leu Glu
    1100                1105                1110

His Tyr Arg Arg Thr His Cys Val Val Ser Glu Leu Ile Ile Gly
    1115                1120                1125

Asn Gly Tyr Tyr Phe Arg Val Phe Ser His Asn Met Val Gly Ser
    1130                1135                1140

Ser Asp Lys Ala Ala Thr Lys Glu Pro Val Phe Ile Pro Arg
    1145                1150                1155

Pro Gly Ile Thr Tyr Glu Pro Pro Lys Tyr Lys Ala Leu Asp Phe
    1160                1165                1170

Ser Glu Ala Pro Ser Phe Thr Gln Pro Leu Ala Asn Arg Ser Ile
    1175                1180                1185

Ile Ala Gly Tyr Asn Ala Ile Leu Cys Cys Ala Val Arg Gly Ser
    1190                1195                1200

Pro Lys Pro Lys Ile Ser Trp Phe Lys Asn Gly Leu Asp Leu Gly
    1205                1210                1215

Glu Asp Ala Arg Phe Arg Met Phe Cys Lys Gln Gly Val Leu Thr
    1220                1225                1230

Leu Glu Ile Arg Lys Pro Cys Pro Tyr Asp Gly Gly Val Tyr Val
    1235                1240                1245

Cys Arg Ala Thr Asn Leu Gln Gly Glu Ala Gln Cys Glu Cys Arg
    1250                1255                1260

Leu Glu Val Arg Val Pro Gln
    1265                1270

<210> SEQ ID NO 6
<211> LENGTH: 1274
<212> TYPE: PRT
<213> ORGANISM: Homo sapiens

<400> SEQUENCE: 6

Met Pro Glu Pro Gly Lys Lys Pro Val Ser Ala Phe Ser Lys Pro
1               5                   10                  15

Arg Ser Val Glu Val Ala Ala Gly Ser Pro Ala Val Phe Glu Ala Glu
            20                  25                  30

Thr Glu Arg Ala Gly Val Lys Val Arg Trp Gln Arg Gly Gly Ser Asp
        35                  40                  45

Ile Ser Ala Ser Asn Lys Tyr Gly Leu Ala Thr Glu Gly Thr Arg His
    50                  55                  60

Thr Leu Thr Val Arg Glu Val Gly Pro Ala Asp Gln Gly Ser Tyr Ala
65                  70                  75                  80

Val Ile Ala Gly Ser Ser Lys Val Lys Phe Asp Leu Lys Val Ile Glu
```

```
                    85                  90                  95
Ala Glu Lys Ala Glu Pro Met Leu Ala Pro Ala Pro Ala Glu
                100                 105                 110
Ala Thr Gly Ala Pro Gly Glu Ala Pro Ala Pro Ala Glu Leu Gly
                115                 120                 125
Glu Ser Ala Pro Ser Pro Lys Gly Ser Ser Ala Ala Leu Asn Gly
            130                 135                 140
Pro Thr Pro Gly Ala Pro Asp Asp Pro Ile Gly Leu Phe Val Met Arg
145                 150                 155                 160
Pro Gln Asp Gly Glu Val Thr Val Gly Gly Ser Ile Thr Phe Ser Ala
                165                 170                 175
Arg Val Ala Gly Ala Ser Leu Leu Lys Pro Pro Val Val Lys Trp Phe
                180                 185                 190
Lys Gly Lys Trp Val Asp Leu Ser Ser Lys Val Gly Gln His Leu Gln
                195                 200                 205
Leu His Asp Ser Tyr Asp Arg Ala Ser Lys Val Tyr Leu Phe Glu Leu
            210                 215                 220
His Ile Thr Asp Ala Gln Pro Ala Phe Thr Gly Ser Tyr Arg Cys Glu
225                 230                 235                 240
Val Ser Thr Lys Asp Lys Phe Asp Cys Ser Asn Phe Asn Leu Thr Val
                245                 250                 255
His Glu Ala Met Gly Thr Gly Asp Leu Asp Leu Leu Ser Ala Phe Arg
            260                 265                 270
Arg Thr Asp Leu Ala Gly Gly Arg Arg Ile Asp Asp Ser His Glu
            275                 280                 285
Asp Thr Gly Ile Leu Asp Phe Ser Ser Leu Leu Lys Lys Arg Asp Asp
            290                 295                 300
Phe Arg Thr Pro Arg Asp Ser Lys Leu Glu Ala Pro Ala Glu Glu Asp
305                 310                 315                 320
Val Trp Glu Ile Leu Arg Gln Ala Pro Pro Ser Glu Tyr Glu Arg Ile
                325                 330                 335
Ala Phe Gln Tyr Gly Val Thr Asp Leu Arg Gly Met Leu Lys Arg Leu
                340                 345                 350
Lys Gly Met Arg Arg Asp Glu Lys Lys Ser Thr Ala Phe Gln Lys Lys
            355                 360                 365
Leu Glu Pro Ala Tyr Gln Val Ser Lys Gly His Lys Ile Arg Leu Thr
            370                 375                 380
Val Glu Leu Ala Asp His Asp Ala Glu Val Lys Trp Leu Lys Asn Gly
385                 390                 395                 400
Gln Glu Ile Gln Met Ser Gly Ser Lys Tyr Ile Phe Glu Ser Ile Gly
                405                 410                 415
Ala Lys Arg Thr Leu Thr Ile Ser Gln Cys Ser Leu Ala Asp Asp Ala
                420                 425                 430
Ala Tyr Gln Cys Val Val Gly Gly Glu Lys Cys Ser Thr Glu Leu Phe
            435                 440                 445
Val Lys Glu Pro Pro Val Leu Ile Thr Arg Pro Leu Glu Asp Gln Leu
450                 455                 460
Val Met Val Gly Gln Arg Val Glu Phe Glu Cys Glu Val Ser Glu Glu
465                 470                 475                 480
Gly Ala Gln Val Lys Trp Leu Lys Asp Gly Val Glu Leu Thr Arg Glu
                485                 490                 495
Glu Thr Phe Lys Tyr Arg Phe Lys Lys Asp Gly Gln Arg His His Leu
            500                 505                 510
```

```
Ile Ile Asn Glu Ala Met Leu Glu Asp Ala Gly His Tyr Ala Leu Cys
            515                 520                 525
Thr Ser Gly Gly Gln Ala Leu Ala Glu Leu Ile Val Gln Glu Lys Lys
530                 535                 540
Leu Glu Val Tyr Gln Ser Ile Ala Asp Leu Met Val Gly Ala Lys Asp
545                 550                 555                 560
Gln Ala Val Phe Lys Cys Glu Val Ser Asp Glu Asn Val Arg Gly Val
                565                 570                 575
Trp Leu Lys Asn Gly Lys Glu Leu Val Pro Asp Ser Arg Ile Lys Val
            580                 585                 590
Ser His Ile Gly Arg Val His Lys Leu Thr Ile Asp Asp Val Thr Pro
        595                 600                 605
Ala Asp Glu Ala Asp Tyr Ser Phe Val Pro Glu Gly Phe Ala Cys Asn
    610                 615                 620
Leu Ser Ala Lys Leu His Phe Met Glu Val Lys Ile Asp Phe Val Pro
625                 630                 635                 640
Arg Gln Glu Pro Pro Lys Ile His Leu Asp Cys Pro Gly Arg Ile Pro
                645                 650                 655
Asp Thr Ile Val Val Ala Gly Asn Lys Leu Arg Leu Asp Val Pro
            660                 665                 670
Ile Ser Gly Asp Pro Ala Pro Thr Val Ile Trp Gln Lys Ala Ile Thr
        675                 680                 685
Gln Gly Asn Lys Ala Pro Ala Arg Pro Ala Pro Asp Ala Pro Glu Asp
    690                 695                 700
Thr Gly Asp Ser Asp Glu Trp Val Phe Asp Lys Lys Leu Leu Cys Glu
705                 710                 715                 720
Thr Glu Gly Arg Val Arg Val Glu Thr Thr Lys Asp Arg Ser Ile Phe
                725                 730                 735
Thr Val Glu Gly Ala Glu Lys Glu Asp Glu Gly Val Tyr Thr Val Thr
            740                 745                 750
Val Lys Asn Pro Val Gly Glu Asp Gln Val Asn Leu Thr Val Lys Val
        755                 760                 765
Ile Asp Val Pro Asp Ala Pro Ala Ala Pro Lys Ile Ser Asn Val Gly
    770                 775                 780
Glu Asp Ser Cys Thr Val Gln Trp Glu Pro Pro Ala Tyr Asp Gly Gly
785                 790                 795                 800
Gln Pro Ile Leu Gly Tyr Ile Leu Glu Arg Lys Lys Lys Ser Tyr
                805                 810                 815
Arg Trp Met Arg Leu Asn Phe Asp Leu Ile Gln Glu Leu Ser His Glu
            820                 825                 830
Ala Arg Arg Met Ile Glu Gly Val Val Tyr Glu Met Arg Val Tyr Ala
        835                 840                 845
Val Asn Ala Ile Gly Met Ser Arg Pro Ser Pro Ala Ser Gln Pro Phe
    850                 855                 860
Met Pro Ile Gly Pro Pro Ser Glu Pro Thr His Leu Ala Val Glu Asp
865                 870                 875                 880
Val Ser Asp Thr Thr Val Ser Leu Lys Trp Arg Pro Pro Glu Arg Val
                885                 890                 895
Gly Ala Gly Gly Leu Asp Gly Tyr Ser Val Glu Tyr Cys Pro Glu Gly
            900                 905                 910
Cys Ser Glu Trp Val Ala Ala Leu Gln Gly Leu Thr Glu His Thr Ser
        915                 920                 925
```

```
Ile Leu Val Lys Asp Leu Pro Thr Gly Ala Arg Leu Leu Phe Arg Val
    930                 935                 940

Arg Ala His Asn Met Ala Gly Pro Gly Ala Pro Val Thr Thr Thr Glu
945                 950                 955                 960

Pro Val Thr Val Gln Glu Ile Leu Gln Arg Pro Arg Leu Gln Leu Pro
                965                 970                 975

Arg His Leu Arg Gln Thr Ile Gln Lys Lys Val Gly Glu Pro Val Asn
            980                 985                 990

Leu Leu Ile Pro Phe Gln Gly Lys Pro Arg Pro Gln Val Thr Trp Thr
        995                 1000                1005

Lys Glu Gly Gln Pro Leu Ala Gly Glu Glu Val Ser Ile Arg Asn
    1010                1015                1020

Ser Pro Thr Asp Thr Ile Leu Phe Ile Arg Ala Ala Arg Arg Val
    1025                1030                1035

His Ser Gly Thr Tyr Gln Val Thr Val Arg Ile Glu Asn Met Glu
    1040                1045                1050

Asp Lys Ala Thr Leu Val Leu Gln Val Val Asp Lys Pro Ser Pro
    1055                1060                1065

Pro Gln Asp Leu Arg Val Thr Asp Ala Trp Gly Leu Asn Val Ala
    1070                1075                1080

Leu Glu Trp Lys Pro Pro Gln Asp Val Gly Asn Thr Glu Leu Trp
    1085                1090                1095

Gly Tyr Thr Val Gln Lys Ala Asp Lys Lys Thr Met Glu Trp Phe
    1100                1105                1110

Thr Val Leu Glu His Tyr Arg Arg Thr His Cys Val Val Pro Glu
    1115                1120                1125

Leu Ile Ile Gly Asn Gly Tyr Tyr Phe Arg Val Phe Ser Gln Asn
    1130                1135                1140

Met Val Gly Phe Ser Asp Arg Ala Ala Thr Thr Lys Glu Pro Val
    1145                1150                1155

Phe Ile Pro Arg Pro Gly Ile Thr Tyr Glu Pro Pro Asn Tyr Lys
    1160                1165                1170

Ala Leu Asp Phe Ser Glu Ala Pro Ser Phe Thr Gln Pro Leu Val
    1175                1180                1185

Asn Arg Ser Val Ile Ala Gly Tyr Thr Ala Met Leu Cys Cys Ala
    1190                1195                1200

Val Arg Gly Ser Pro Lys Pro Lys Ile Ser Trp Phe Lys Asn Gly
    1205                1210                1215

Leu Asp Leu Gly Glu Asp Ala Arg Phe Arg Met Phe Ser Lys Gln
    1220                1225                1230

Gly Val Leu Thr Leu Glu Ile Arg Lys Pro Cys Pro Phe Asp Gly
    1235                1240                1245

Gly Ile Tyr Val Cys Arg Ala Thr Asn Leu Gln Gly Glu Ala Arg
    1250                1255                1260

Cys Glu Cys Arg Leu Glu Val Arg Val Pro Gln
    1265                1270

<210> SEQ ID NO 7
<211> LENGTH: 1270
<212> TYPE: PRT
<213> ORGANISM: Mus musculus

<400> SEQUENCE: 7

Met Pro Glu Pro Gly Lys Lys Pro Val Ser Ala Phe Asn Lys Lys Pro
1               5                   10                  15
```

```
Arg Ser Ala Glu Val Thr Ala Gly Ser Ala Ala Val Phe Glu Ala Gly
            20                  25                  30

Thr Glu Arg Ser Gly Val Lys Val Arg Trp Gln Arg Asp Gly Ser Asp
        35                  40                  45

Ile Thr Ala Asn Asp Lys Tyr Gly Leu Ala Ala Glu Gly Lys Arg His
 50                  55                  60

Thr Leu Thr Val Arg Asp Ala Ser Pro Asp Gln Gly Ser Tyr Ala
 65                  70                  75                  80

Val Ile Ala Gly Ser Ser Lys Val Lys Phe Asp Leu Lys Val Thr Glu
                85                  90                  95

Pro Ala Pro Pro Glu Lys Ala Glu Ser Glu Val Ala Pro Gly Ala Pro
               100                 105                 110

Lys Glu Val Pro Ala Pro Ala Thr Glu Leu Glu Glu Ser Val Ser Ser
           115                 120                 125

Pro Glu Gly Ser Val Ser Val Thr Gln Asp Gly Ser Ala Ala Glu His
       130                 135                 140

Gln Gly Ala Pro Asp Asp Pro Ile Gly Leu Phe Leu Met Arg Pro Gln
145                 150                 155                 160

Asp Gly Glu Val Thr Val Gly Gly Ser Ile Val Phe Ser Ala Arg Val
                165                 170                 175

Ala Gly Ala Ser Leu Leu Lys Pro Pro Val Val Lys Trp Phe Lys Gly
            180                 185                 190

Lys Trp Val Asp Leu Ser Ser Lys Val Gly Gln His Leu Gln Leu His
        195                 200                 205

Asp Ser Tyr Asp Arg Ala Ser Lys Val Tyr Leu Phe Glu Leu His Ile
    210                 215                 220

Thr Asp Ala Gln Thr Thr Ser Ala Gly Gly Tyr Arg Cys Glu Val Ser
225                 230                 235                 240

Thr Lys Asp Lys Phe Asp Ser Cys Ser Phe Asn Leu Thr Val His Glu
                245                 250                 255

Ala Ile Gly Ser Gly Asp Leu Asp Leu Arg Ser Ala Phe Arg Arg Thr
            260                 265                 270

Ala Leu Ala Gly Ala Gly Arg Arg Thr Ala Asp Ser His Glu Asp Ala
        275                 280                 285

Gly Thr Leu Asp Phe Ser Ser Leu Leu Lys Lys Arg Asp Ala Phe Arg
    290                 295                 300

Arg Asp Ser Lys Leu Glu Ala Pro Ala Glu Glu Asp Val Trp Glu Ile
305                 310                 315                 320

Leu Arg Gln Ala Pro Pro Ser Glu Tyr Glu Arg Ile Ala Phe Gln His
                325                 330                 335

Gly Val Thr Asp Leu Arg Gly Met Leu Lys Arg Leu Lys Gly Met Lys
            340                 345                 350

Gln Asp Glu Lys Lys Ser Thr Ala Phe Gln Lys Lys Leu Glu Pro Ala
        355                 360                 365

Tyr Gln Val Asn Lys Gly His Lys Ile Arg Leu Thr Val Glu Leu Ala
    370                 375                 380

Asp Pro Asp Ala Glu Val Lys Trp Leu Lys Asn Gly Gln Glu Ile Gln
385                 390                 395                 400

Met Ser Gly Ser Lys Tyr Ile Phe Glu Ser Val Gly Ala Lys Arg Thr
                405                 410                 415

Leu Thr Ile Ser Gln Cys Ser Leu Ala Asp Asp Ala Ala Tyr Gln Cys
            420                 425                 430
```

-continued

```
Val Val Gly Gly Glu Lys Cys Ser Thr Glu Leu Phe Lys Glu Pro
            435                 440                 445
Pro Val Leu Ile Thr Arg Ser Leu Glu Asp Gln Leu Val Met Val Gly
450                 455                 460
Gln Arg Val Glu Phe Glu Cys Glu Val Ser Glu Glu Gly Ala Gln Val
465                 470                 475                 480
Lys Trp Leu Lys Asp Gly Val Glu Leu Thr Arg Glu Thr Phe Lys
                485                 490                 495
Tyr Arg Phe Lys Lys Asp Gly Arg Lys His His Leu Ile Ile Asn Glu
                500                 505                 510
Ala Thr Leu Glu Asp Ala Gly His Tyr Ala Val Arg Thr Ser Gly Gly
            515                 520                 525
Gln Ser Leu Ala Glu Leu Ile Val Gln Glu Lys Lys Leu Glu Val Tyr
530                 535                 540
Gln Ser Ile Ala Asp Leu Ala Val Gly Ala Lys Asp Gln Ala Val Phe
545                 550                 555                 560
Lys Cys Glu Val Ser Asp Glu Asn Val Arg Gly Val Trp Leu Lys Asn
                565                 570                 575
Gly Lys Glu Leu Val Pro Asp Asn Arg Ile Lys Val Ser His Ile Gly
            580                 585                 590
Arg Val His Lys Leu Thr Ile Asp Asp Val Thr Pro Ala Asp Glu Ala
            595                 600                 605
Asp Tyr Ser Phe Val Pro Glu Gly Phe Ala Cys Asn Leu Ser Ala Lys
            610                 615                 620
Leu His Phe Met Glu Val Lys Ile Asp Phe Val Pro Arg Gln Glu Pro
625                 630                 635                 640
Pro Lys Ile His Leu Asp Cys Pro Gly Ser Thr Pro Asp Thr Ile Val
                645                 650                 655
Val Val Ala Gly Asn Lys Leu Arg Leu Asp Val Pro Ile Ser Gly Asp
                660                 665                 670
Pro Ala Pro Thr Val Val Trp Gln Lys Thr Val Thr Gln Gly Lys Lys
            675                 680                 685
Ala Ser Thr Gly Pro His Pro Asp Ala Pro Glu Asp Ala Gly Ala Asp
690                 695                 700
Glu Glu Trp Val Phe Asp Lys Lys Leu Leu Cys Glu Thr Glu Gly Arg
705                 710                 715                 720
Val Arg Val Glu Thr Thr Lys Asp Arg Ser Val Phe Thr Val Glu Gly
                725                 730                 735
Ala Gly Lys Glu Asp Glu Gly Val Tyr Thr Val Thr Val Lys Asn Pro
            740                 745                 750
Val Gly Glu Asp Gln Val Asn Leu Thr Val Lys Val Ile Asp Val Pro
            755                 760                 765
Asp Ala Pro Ala Ala Pro Lys Ile Ser Asn Val Gly Glu Asp Ser Cys
770                 775                 780
Thr Val Gln Trp Glu Pro Pro Ala Tyr Asp Gly Gly Gln Pro Val Leu
785                 790                 795                 800
Gly Tyr Ile Leu Glu Arg Lys Lys Lys Ser Tyr Arg Trp Met Arg
                805                 810                 815
Leu Asn Phe Asp Leu Leu Arg Glu Leu Ser His Glu Ala Arg Arg Met
                820                 825                 830
Ile Glu Gly Val Ala Tyr Glu Met Arg Val Tyr Ala Val Asn Ala Val
            835                 840                 845
Gly Met Ser Arg Pro Ser Pro Ala Ser Gln Pro Phe Met Pro Ile Gly
```

```
                850               855               860
Pro Pro Gly Glu Pro Thr His Leu Ala Val Glu Asp Val Ser Asp Thr
865               870               875               880

Thr Val Ser Leu Lys Trp Arg Pro Glu Arg Val Gly Ala Gly Gly
            885               890               895

Leu Asp Gly Tyr Ser Val Glu Tyr Cys Gln Glu Gly Cys Ser Glu Trp
            900               905               910

Thr Pro Ala Leu Gln Gly Leu Thr Glu Arg Thr Ser Met Leu Val Lys
            915               920               925

Asp Leu Pro Thr Gly Ala Arg Leu Leu Phe Arg Val Arg Ala His Asn
            930               935               940

Val Ala Gly Pro Gly Gly Pro Ile Val Thr Lys Glu Pro Val Thr Val
945               950               955               960

Gln Glu Ile Leu Gln Arg Pro Arg Leu Gln Leu Pro Arg His Leu Arg
            965               970               975

Gln Thr Ile Gln Lys Lys Val Gly Glu Pro Val Asn Leu Leu Ile Pro
            980               985               990

Phe Gln Gly Lys Pro Arg Pro Gln Val Thr Trp Thr Lys Glu Gly Gln
            995              1000              1005

Pro Leu Ala Gly Glu Glu Val Ser Ile Arg Asn Ser Pro Thr Asp
       1010              1015              1020

Thr Ile Leu Phe Ile Arg Ala Ala Arg Arg Thr His Ser Gly Thr
       1025              1030              1035

Tyr Gln Val Thr Val Arg Ile Glu Asn Met Glu Asp Lys Ala Thr
       1040              1045              1050

Leu Ile Leu Gln Ile Val Asp Lys Pro Ser Pro Pro Gln Asp Ile
       1055              1060              1065

Arg Ile Val Glu Thr Trp Gly Phe Asn Val Ala Leu Glu Trp Lys
       1070              1075              1080

Pro Pro Gln Asp Asp Gly Asn Thr Glu Ile Trp Gly Tyr Thr Val
       1085              1090              1095

Gln Lys Ala Asp Lys Lys Thr Met Glu Trp Phe Thr Val Leu Glu
       1100              1105              1110

His Tyr Arg Arg Thr His Cys Val Val Ser Glu Leu Ile Ile Gly
       1115              1120              1125

Asn Gly Tyr Tyr Phe Arg Val Phe Ser His Asn Met Val Gly Ser
       1130              1135              1140

Ser Asp Lys Ala Ala Ala Thr Lys Glu Pro Val Phe Ile Pro Arg
       1145              1150              1155

Pro Gly Ile Thr Tyr Glu Pro Pro Lys Tyr Lys Ala Leu Asp Phe
       1160              1165              1170

Ser Glu Ala Pro Ser Phe Thr Gln Pro Leu Ala Asn Arg Ser Ile
       1175              1180              1185

Ile Ala Gly Tyr Asn Ala Ile Leu Cys Cys Ala Val Arg Gly Ser
       1190              1195              1200

Pro Lys Pro Lys Ile Ser Trp Phe Lys Asn Gly Leu Asp Leu Gly
       1205              1210              1215

Glu Asp Ala Arg Phe Arg Met Phe Cys Lys Gln Gly Val Leu Thr
       1220              1225              1230

Leu Glu Ile Arg Lys Pro Cys Pro Tyr Asp Gly Gly Val Tyr Val
       1235              1240              1245

Cys Arg Ala Thr Asn Leu Gln Gly Glu Ala Gln Cys Glu Cys Arg
       1250              1255              1260
```

```
Leu Glu   Val Arg Val Pro Gln
    1265              1270

<210> SEQ ID NO 8
<211> LENGTH: 1274
<212> TYPE: PRT
<213> ORGANISM: Homo sapiens

<400> SEQUENCE: 8

Met Pro Glu Pro Gly Lys Lys Pro Val Ser Ala Phe Ser Lys Lys Pro
1               5                   10                  15

Arg Ser Val Glu Val Ala Ala Gly Ser Pro Ala Val Phe Glu Ala Glu
            20                  25                  30

Thr Glu Arg Ala Gly Val Lys Val Arg Trp Gln Arg Gly Gly Ser Asp
        35                  40                  45

Ile Ser Ala Ser Asn Lys Tyr Gly Leu Ala Thr Glu Gly Thr Arg His
    50                  55                  60

Thr Leu Thr Val Arg Glu Val Gly Pro Ala Asp Gln Gly Ser Tyr Ala
65                  70                  75                  80

Val Ile Ala Gly Ser Ser Lys Val Lys Phe Asp Leu Lys Val Ile Glu
                85                  90                  95

Ala Glu Lys Ala Glu Pro Met Leu Ala Pro Ala Pro Ala Pro Ala Glu
            100                 105                 110

Ala Thr Gly Ala Pro Gly Glu Ala Pro Ala Pro Ala Ala Glu Leu Gly
        115                 120                 125

Glu Ser Ala Pro Ser Pro Lys Gly Ser Ser Ser Ala Ala Leu Asn Gly
    130                 135                 140

Pro Thr Pro Gly Ala Pro Asp Asp Pro Ile Gly Leu Phe Val Met Arg
145                 150                 155                 160

Pro Gln Asp Gly Glu Val Thr Val Gly Gly Ser Ile Thr Phe Ser Ala
                165                 170                 175

Arg Val Ala Gly Ala Ser Leu Leu Lys Pro Pro Val Val Lys Trp Phe
            180                 185                 190

Lys Gly Lys Trp Val Asp Leu Ser Ser Lys Val Gly Gln His Leu Gln
        195                 200                 205

Leu His Asp Ser Tyr Asp Arg Ala Ser Lys Val Tyr Leu Phe Glu Leu
    210                 215                 220

His Ile Thr Asp Ala Gln Pro Ala Phe Thr Gly Ser Tyr Arg Cys Glu
225                 230                 235                 240

Val Ser Thr Lys Asp Lys Phe Asp Cys Ser Asn Phe Asn Leu Thr Val
                245                 250                 255

His Glu Ala Met Gly Thr Gly Asp Leu Asp Leu Leu Ser Ala Phe Arg
            260                 265                 270

Arg Thr Ala Leu Ala Gly Gly Arg Arg Ile Ala Asp Ser His Glu
        275                 280                 285

Asp Thr Gly Ile Leu Asp Phe Ser Ser Leu Leu Lys Lys Arg Asp Ala
    290                 295                 300

Phe Arg Thr Pro Arg Asp Ser Lys Leu Glu Ala Pro Ala Glu Glu Asp
305                 310                 315                 320

Val Trp Glu Ile Leu Arg Gln Ala Pro Pro Ser Glu Tyr Glu Arg Ile
                325                 330                 335

Ala Phe Gln Tyr Gly Val Thr Asp Leu Arg Gly Met Leu Lys Arg Leu
            340                 345                 350

Lys Gly Met Arg Arg Asp Glu Lys Lys Ser Thr Ala Phe Gln Lys Lys
```

```
                355                 360                 365
Leu Glu Pro Ala Tyr Gln Val Ser Lys Gly His Lys Ile Arg Leu Thr
    370                 375                 380
Val Glu Leu Ala Asp His Asp Ala Glu Val Lys Trp Leu Lys Asn Gly
385                 390                 395                 400
Gln Glu Ile Gln Met Ser Gly Ser Lys Tyr Ile Phe Glu Ser Ile Gly
                405                 410                 415
Ala Lys Arg Thr Leu Thr Ile Ser Gln Cys Ser Leu Ala Asp Asp Ala
            420                 425                 430
Ala Tyr Gln Cys Val Val Gly Glu Lys Cys Ser Thr Glu Leu Phe
        435                 440                 445
Val Lys Glu Pro Pro Val Leu Ile Thr Arg Pro Leu Glu Asp Gln Leu
    450                 455                 460
Val Met Val Gly Gln Arg Val Glu Phe Glu Cys Glu Val Ser Glu Glu
465                 470                 475                 480
Gly Ala Gln Val Lys Trp Leu Lys Asp Gly Val Glu Leu Thr Arg Glu
                485                 490                 495
Glu Thr Phe Lys Tyr Arg Phe Lys Lys Asp Gly Gln Arg His His Leu
            500                 505                 510
Ile Ile Asn Glu Ala Met Leu Glu Asp Ala Gly His Tyr Ala Leu Cys
        515                 520                 525
Thr Ser Gly Gly Gln Ala Leu Ala Glu Leu Ile Val Gln Glu Lys Lys
    530                 535                 540
Leu Glu Val Tyr Gln Ser Ile Ala Asp Leu Met Val Gly Ala Lys Asp
545                 550                 555                 560
Gln Ala Val Phe Lys Cys Glu Val Ser Asp Glu Asn Val Arg Gly Val
                565                 570                 575
Trp Leu Lys Asn Gly Lys Glu Leu Val Pro Asp Ser Arg Ile Lys Val
            580                 585                 590
Ser His Ile Gly Arg Val His Lys Leu Thr Ile Asp Asp Val Thr Pro
        595                 600                 605
Ala Asp Glu Ala Asp Tyr Ser Phe Val Pro Glu Gly Phe Ala Cys Asn
    610                 615                 620
Leu Ser Ala Lys Leu His Phe Met Glu Val Lys Ile Asp Phe Val Pro
625                 630                 635                 640
Arg Gln Glu Pro Pro Lys Ile His Leu Asp Cys Pro Gly Arg Ile Pro
                645                 650                 655
Asp Thr Ile Val Val Ala Gly Asn Lys Leu Arg Leu Asp Val Pro
            660                 665                 670
Ile Ser Gly Asp Pro Ala Pro Thr Val Ile Trp Gln Lys Ala Ile Thr
        675                 680                 685
Gln Gly Asn Lys Ala Pro Ala Arg Pro Ala Pro Asp Ala Pro Glu Asp
    690                 695                 700
Thr Gly Asp Ser Asp Glu Trp Val Phe Asp Lys Lys Leu Leu Cys Glu
705                 710                 715                 720
Thr Glu Gly Arg Val Arg Val Glu Thr Thr Lys Asp Arg Ser Ile Phe
                725                 730                 735
Thr Val Glu Gly Ala Glu Lys Glu Asp Glu Gly Val Tyr Thr Val Thr
            740                 745                 750
Val Lys Asn Pro Val Gly Glu Asp Gln Val Asn Leu Thr Val Lys Val
        755                 760                 765
Ile Asp Val Pro Asp Ala Pro Ala Ala Pro Lys Ile Ser Asn Val Gly
    770                 775                 780
```

```
Glu Asp Ser Cys Thr Val Gln Trp Glu Pro Pro Ala Tyr Asp Gly Gly
785                 790                 795                 800

Gln Pro Ile Leu Gly Tyr Ile Leu Glu Arg Lys Lys Lys Ser Tyr
                805                 810                 815

Arg Trp Met Arg Leu Asn Phe Asp Leu Ile Gln Glu Leu Ser His Glu
                820                 825                 830

Ala Arg Arg Met Ile Glu Gly Val Val Tyr Glu Met Arg Val Tyr Ala
                835                 840                 845

Val Asn Ala Ile Gly Met Ser Arg Pro Ser Pro Ala Ser Gln Pro Phe
850                 855                 860

Met Pro Ile Gly Pro Pro Ser Glu Pro Thr His Leu Ala Val Glu Asp
865                 870                 875                 880

Val Ser Asp Thr Thr Val Ser Leu Lys Trp Arg Pro Pro Glu Arg Val
                885                 890                 895

Gly Ala Gly Gly Leu Asp Gly Tyr Ser Val Glu Tyr Cys Pro Glu Gly
                900                 905                 910

Cys Ser Glu Trp Val Ala Ala Leu Gln Gly Leu Thr Glu His Thr Ser
                915                 920                 925

Ile Leu Val Lys Asp Leu Pro Thr Gly Ala Arg Leu Leu Phe Arg Val
                930                 935                 940

Arg Ala His Asn Met Ala Gly Pro Gly Ala Pro Val Thr Thr Thr Glu
945                 950                 955                 960

Pro Val Thr Val Gln Glu Ile Leu Gln Arg Pro Arg Leu Gln Leu Pro
                965                 970                 975

Arg His Leu Arg Gln Thr Ile Gln Lys Lys Val Gly Glu Pro Val Asn
                980                 985                 990

Leu Leu Ile Pro Phe Gln Gly Lys Pro Arg Pro Gln Val Thr Trp Thr
                995                 1000                1005

Lys Glu Gly Gln Pro Leu Ala Gly Glu Glu Val Ser Ile Arg Asn
1010                1015                1020

Ser Pro Thr Asp Thr Ile Leu Phe Ile Arg Ala Ala Arg Arg Val
1025                1030                1035

His Ser Gly Thr Tyr Gln Val Thr Val Arg Ile Glu Asn Met Glu
1040                1045                1050

Asp Lys Ala Thr Leu Val Leu Gln Val Val Asp Lys Pro Ser Pro
1055                1060                1065

Pro Gln Asp Leu Arg Val Thr Asp Ala Trp Gly Leu Asn Val Ala
1070                1075                1080

Leu Glu Trp Lys Pro Pro Gln Asp Val Gly Asn Thr Glu Leu Trp
1085                1090                1095

Gly Tyr Thr Val Gln Lys Ala Asp Lys Lys Thr Met Glu Trp Phe
1100                1105                1110

Thr Val Leu Glu His Tyr Arg Arg Thr His Cys Val Val Pro Glu
1115                1120                1125

Leu Ile Ile Gly Asn Gly Tyr Tyr Phe Arg Val Phe Ser Gln Asn
1130                1135                1140

Met Val Gly Phe Ser Asp Arg Ala Ala Thr Thr Lys Glu Pro Val
1145                1150                1155

Phe Ile Pro Arg Pro Gly Ile Thr Tyr Glu Pro Pro Asn Tyr Lys
1160                1165                1170

Ala Leu Asp Phe Ser Glu Ala Pro Ser Phe Thr Gln Pro Leu Val
1175                1180                1185
```

-continued

```
Asn Arg Ser Val Ile Ala Gly Tyr Thr Ala Met Leu Cys Cys Ala
    1190            1195            1200

Val Arg Gly Ser Pro Lys Pro Lys Ile Ser Trp Phe Lys Asn Gly
    1205            1210            1215

Leu Asp Leu Gly Glu Asp Ala Arg Phe Arg Met Phe Ser Lys Gln
    1220            1225            1230

Gly Val Leu Thr Leu Glu Ile Arg Lys Pro Cys Pro Phe Asp Gly
    1235            1240            1245

Gly Ile Tyr Val Cys Arg Ala Thr Asn Leu Gln Gly Glu Ala Arg
    1250            1255            1260

Cys Glu Cys Arg Leu Glu Val Arg Val Pro Gln
    1265            1270

<210> SEQ ID NO 9
<211> LENGTH: 25
<212> TYPE: DNA
<213> ORGANISM: Mus musculus

<400> SEQUENCE: 9
atgccggagc cagggaagaa accag                                             25

<210> SEQ ID NO 10
<211> LENGTH: 24
<212> TYPE: DNA
<213> ORGANISM: Mus musculus

<400> SEQUENCE: 10
tcactgagga actcgcacct ccag                                              24
```

METHODS OF TREATING CARDIOMYOPATHY

RELATED APPLICATION

This application claims priority from U.S. Provisional Application No. 61/537,425, filed Sep. 21, 2011, the subject matter of which is incorporated herein by reference in its entirety.

TECHNICAL FIELD

This application relates to methods and agents for the treatment of cardiomyopathies in a subject and particularly relates to methods and agents for the treatment of hypertrophic cardiomyopathy.

BACKGROUND

Familial hypertrophic cardiomyopathy (FHC) is an inherited autosomal trait that is most commonly caused by mutations in sarcomeric protein genes. Of the 10 different sarcomeric genes identified to cause hypertrophic cardiomyopathy (HCM), mutations in cardiac myosin binding protein C (cMyBPC) are among the most common of all known hereditary linked HCM. FHC impacts approximately 1 in 500 individuals; however, several founding mutations in cMyBPC in different regions of the world have been recently shown to affect disproportionally large numbers of families from common ancestry who are at significantly greater risk for development of cardiac dysfunction and heart failure compared to the individual who do not carry these mutations. In the last 15 years, approximately 200 disease causing cMyBPC mutations have been identified, which have been associated with variable degrees of contractile dysfunction and hypertrophy. The majorities of cMyBPC mutations are heterozygous and have variable clinical presentation, but homozygous mutations are associated with severe hypertrophy and high mortality rates at a young age.

SUMMARY

Embodiments of this application relate to a method of treating a cardiomyopathy, such as hypertrophic cardiomyopathy (HCM) or familial hypertrophic cardiomyopathy (FHC), in a subject. The method includes administering to the subject a therapeutically effective amount of an agent that modulates contractile function in myocardial tissue of the subject. The agent can includes a nucleic acid encoding a cMyBPC protein or a mutant, variant, or fragment of a cMyBPC protein that can increase or decrease the contractile function of the myocardium.

In some aspects, the agent can include nucleic acids that can be used to express wild type cMyBPC protein having an amino acid sequence of SEQ ID NO: 1 or SEQ ID NO: 2. In other aspects, the agent can include a nucleic acid that can be used to express a variant cMyBPC protein, which has a triple S to D phosphorylation mutation. The variant cMyBPC protein, which has a triple S to D mutation, when expressed in myocardial tissue can increase contractile function of the myocardium. The S to D phosphorylation mutation can be S273D, S282D, and 5302D for SEQ ID NO: 1 and S275D, S284D, and 5304D for SEQ ID NO: 2. The variant cMyBPC proteins expressed with the S to D mutation can have an amino acid sequence of SEQ ID NO: 5 or SEQ ID NO: 6.

In still other aspects, the agent can include a nucleic acid that can be used to express a variant cMyBPC protein, which includes a triple S to A mutation. The variant cMyBPC protein, which has a triple S to A mutation, when expressed in myocardial tissue can decrease contractile function of the myocardium. The S to A phosphorylation mutation can be S273A, S282A, and S302A for SEQ ID NO: 1 and S275A, S284A, and S304A for SEQ ID NO: 2. The variant cMyBPC proteins expressed with the S to A mutation can have an amino acid sequence of SEQ ID NO: 7 or SEQ ID NO: 8.

In some aspects, the agent includes a vector that can transfect the cells and facilitate expression of the nucleic acid encoding a cMyBPC protein or variant thereof in myocardial tissue of the subject. The agent can be administered directly to the atrium or myocardial tissue of the subject. The myocardial tissue can include left ventricle cardiac tissue. The agent can be administered to the subject's myocardial tissue at an amount effective to cause functional improvement in at least one parameter of the myocardium selected from the group consisting of fractional shortening, ejection fraction, and ejection time, left ventricular weight, and end diastolic and systolic chamber dimensions.

BRIEF DESCRIPTION OF THE DRAWINGS

FIG. 1 illustrates images of 10% SDS-PAGE coomassie stained (left) or 12% SDS-PAGE Pro-Q Diamond stained gels (right) depicting protein expression in skinned myocardium isolated from WT (lane 1), LcMyBPC treated cMyBPC$^{-/-}$ (lane 2), and untreated cMyBPC$^{-/-}$ hearts (lane 3).

FIG. 2 illustrates histograms showing phosphorylation analysis of Pro-Q Diamond stained gels. Slopes of phosphorylation signals from Pro-Q Diamond stained gels (n=4) determined from regression analysis of plots of area average optical density versus protein loaded (μg). Myocardium was isolated from hearts of: lane 1: WT, lane 2: LcMyBPC treated cMyBPC$^{-/-}$, lane 3: cMyBPC−/− mice. Data are means SE.

FIGS. 3(A-B) illustrate (A) western blots of skinned myocardium that was used for mechanical experiments probed with a cMyBPC specific antibody; lane 1: WT, lane 2: cMyBPC$^{-/-}$, lane 3: LcMyBPC treated cMyBPC$^{-/-}$ (21 days), lane 4: LcMyBPC treated cMyBPC$^{-/-}$ (20 weeks), lane 5: vehicle treated cMyBPC$^{-/-}$. α-actinin was quantified as a loading control (bottom row); and (B) 6% SDS-PAGE silver stained gel depicting myosin heavy chain isoform expression in myocardium isolated from: lane 1: WT, lane 2: cMyBPC$^{-/-}$, lane 3: LcMyBPC treated cMyBPC$^{-/-}$ hearts.

FIGS. 6(A-D) illustrate plots showing steady-state isometric force (A and B) was measured as a function of pCa and the apparent rate constant of force development (ktr) after rapid release-restretch protocol (C and D) was plotted as a function of relative isometric steady-state force (P/Po) in skinned myocardium isolated from WT (circles), untreated cMyBPC$^{-/-}$ (triangles), cMyBPC$^{-/-}$ following cMyBPC gene transfer (LcMyBPC, squares, panels A and C) hearts, and in vitro reconstitution of cMyBPC$^{-/-}$ skinned myocardium with recombinant cMyBPC (cMyBPC, squares, panels B and D). Values are means SE from 16-20 experiments.

FIGS. 7(A-C) illustrate plots showing the effects of in vivo cMyBPC gene transfer on cross-bridge kinetics. Force transients following a stretch of 1% of muscle length recorded at $[Ca^{2+}]$ yielding a pre-stretch isometric force of ~50% maximal in skinned myocardium isolated from (A) untreated cMyBPC$^{-/-}$ and LcMyBPC treated cMyBPC$^{-/-}$ hearts, (B) untreated cMyBPC$^{-/-}$ and LCMV treated cMyBPC$^{-/-}$ hearts, and (C) WT and LcMyBPC treated cMyBPC/hearts. These representative transients are normalized to pre-stretch isometric force corresponding to the force base-line, which is arbitrarily set at zero.

FIGS. 8(A-C) illustrate two dimensional echocardiography images acquired in M-mode along the parasternal short-axis view showing contractility of (A)WT, (B) LcMyBPC treated cMyBPC$^{-/-}$, and (C) untreated cMyBPC$^{-/-}$ hearts. ESD: End-systolic dimension, EDD: end-diastolic dimension. cMyBPC expression in the LcMyBPC treated cMyBPC$^{-/-}$ heart that is depicted was 96% of WT levels.

FIGS. 10(A-D) illustrate confocal images of immunohistochemical staining of cMyBPC in mid-ventricular slices isolated from LcMyBPC treated (left) and untreated (right) cMyBPC$^{-/-}$ hearts. (A-B): left-ventricular slices prepared from the apex (C), mid-ventricle (D), and base (E) of a cMyBPC-/- heart treated with LcMyBPC (60× magnification).

DETAILED DESCRIPTION

Figure 4:
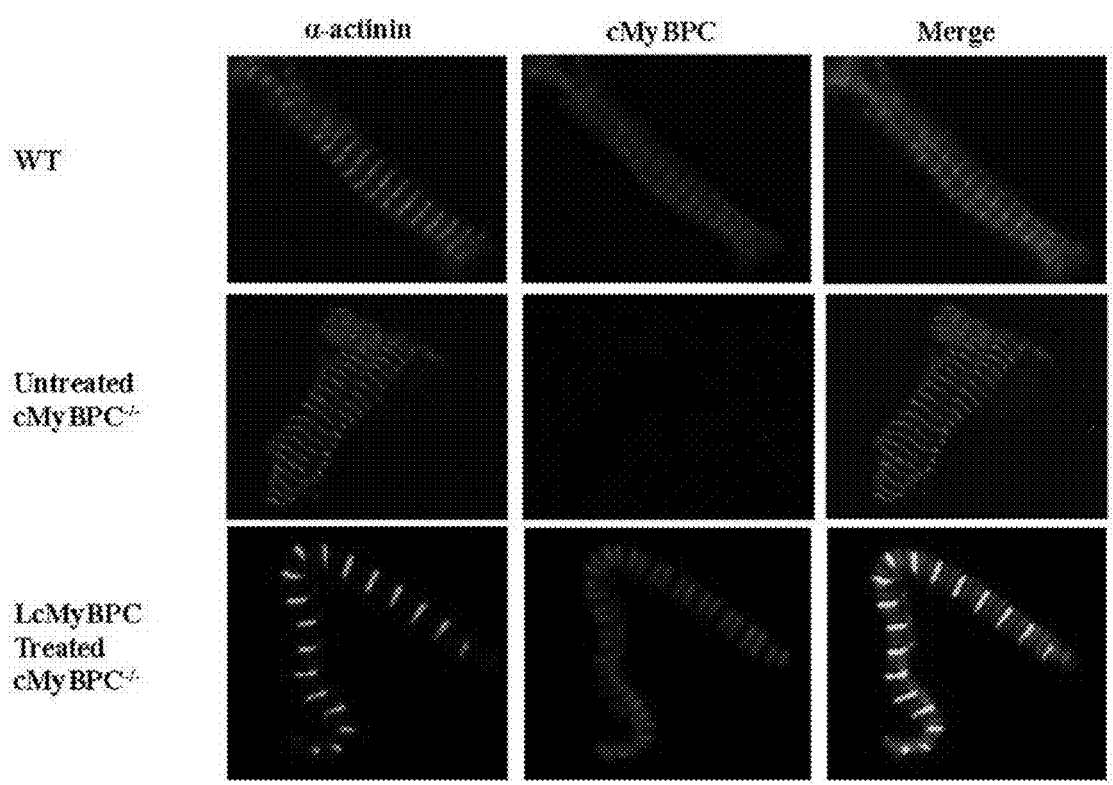
FIG. 4 illustrates confocal images (100× magnification) of skinned myocardium isolated from WT, untreated cMyBPC$^{-/-}$, LcMyBPC treated cMyBPC$^{-/-}$ hearts. Immunohistochemistry was used to demonstrate the localization of α-actinin (green) and cMyBPC (red) within the sarcomere.

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety. In the event that there is a plurality of definitions for terms herein, those in this section prevail. Unless otherwise defined, all technical terms used herein have the same meaning as commonly understood by one of ordinary skill in the art to which this invention belongs. Commonly understood definitions of molecular biology terms can be found in, for example, Rieger et al., Glossary of Genetics: Classical and Molecular, 5th edition, Springer-Verlag: New York, 1991; and Lewin, Genes V, Oxford University Press: New York, 1994.

Methods involving conventional molecular biology techniques are described herein. Such techniques are generally known in the art and are described in detail in methodology treatises, such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22:1859-1862, 1981, and Matteucci et al., J. Am. Chem. Soc. 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

As used herein, the term "nucleic acid" refers to a polynucleotide containing at least two covalently linked nucleotide or nucleotide analog subunits. A nucleic acid can be a deoxyribonucleic acid (DNA), a ribonucleic acid (RNA), or an analog of DNA or RNA. Nucleotide analogs are commercially available and methods of preparing polynucleotides containing such nucleotide analogs are known (Lin et al. (1994) Nucl. Acids Res. 22:5220-5234; Jellinek et al. (1995) Biochemistry 34:11363-11372; Pagratis et al. (1997) Nature Biotechnol. 15:68-73). The nucleic acid can be single-stranded, double-stranded, or a mixture thereof. For purposes herein, unless specified otherwise, the nucleic acid is double-stranded, or it is apparent from the context.

As used herein, the term "DNA" is meant to include all types and sizes of DNA molecules including cDNA, plasmids and DNA including modified nucleotides and nucleotide analogs.

As used herein, the term "nucleotides" include nucleoside mono-, di-, and triphosphates. Nucleotides also include modified nucleotides, such as, but are not limited to, phosphorothioate nucleotides and deazapurine nucleotides and other nucleotide analogs. The terms "polynucleotide sequence" and "nucleotide sequence" are also used interchangeably herein.

As used herein, the term "isolated" with respect to nucleic acids, such as DNA or RNA, refers to molecules separated from other DNAs, or RNAs, respectively, which are present in the natural source of the macromolecule. The term isolated as used herein also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragments, which are not naturally occurring as fragments and would not be found in the natural state.

As used herein, the term "wild type" refers to the naturally-occurring polynucleotide sequence encoding a protein, or a portion thereof, or protein sequence, or portion thereof, respectively, as it normally exists in vivo in normal or healthy subject.

As used herein, the term "mutant" refers to changes in the genetic material of an organism, in particular a change (i.e., deletion, substitution, addition, or alteration) in a wild type polynucleotide sequence or changes in a wild type protein. The term "variant" is used interchangeably with "mutant" and is also intended to include functional "fragments" of the protein mutant or variant. Although it is often assumed that a change in the genetic material results in a change of the function of the protein, the terms "mutant" and "variant" refer to a change in the sequence of a wild type protein regardless of whether that change alters the function of the protein (e.g., increases, decreases, imparts a new function), or whether that change has no effect on the function of the protein (e.g., the mutation or variation is silent).

As used herein, the term "protein" refers to a polymer consisting of the 20 amino acids. Although "polypeptide" is often used in reference to relatively large polypeptides, and "peptide" is often used in reference to small polypeptides, usage of these terms in the art overlaps and is varied. The term "recombinant protein" as used herein, means that a protein is derived from a prokaryotic or eukaryotic expression system.

As used herein, the term "chimeric protein" or "fusion protein" refers to a fusion of a first amino acid sequence encoding a polypeptide with a second amino acid sequence defining a domain (e.g., polypeptide portion) foreign to and not substantially homologous with the domain of the first polypeptide. A chimeric protein may present a foreign domain which is found (albeit in a different protein) in an organism which also expresses the first protein, or it may be an "interspecies", "intergenic", etc. fusion of protein structures expressed by different kinds of organisms.

As used herein, the term "vector" refers to a nucleic acid molecule capable of transporting another nucleic acid to which it has been linked. Preferred vectors are those capable of one or more of, autonomous replication and expression of nucleic acids to which they are linked. Vectors capable of directing the expression of genes to which they are operatively linked are referred to herein as "expression vectors".

As used herein, a polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

As used herein, "transcriptional regulatory sequence" is a generic term that refers to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences, which control transcription of the naturally occurring form of a protein.

As used herein, the term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue, such as myocytes or myocardial cells. The term also covers so-called "leaky" promoters, which regulate expression of a selected nucleic acid primarily in one tissue, but cause expression in other tissues as well.

As used herein, the terms "homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

As used herein, the term "delivery," which is used interchangeably with "transduction," refers to the process by which exogenous nucleic acid molecules are transferred into a cell such that they are located inside the cell. Delivery of nucleic acids is a distinct process from expression of nucleic acids.

As used herein, a "multiple cloning site (MCS)" is a nucleic acid region in a plasmid that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector.

As used herein, the term "origin of replication" (often termed "ori"), refers to a specific nucleic acid sequence at which replication is initiated. Alternatively, an autonomously replicating sequence (ARS) can be employed if the host cell is yeast.

As used herein, "selectable or screenable markers" confer an identifiable change to a cell permitting easy identification of cells containing an expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

As used herein, the term "gene" or "recombinant gene" refers to a nucleic acid comprising an open reading frame encoding a polypeptide, including both exon and (optionally) intron sequences.

As used herein, the term "transfection" refers to the uptake of foreign DNA by a cell. A cell has been "transfected" when exogenous DNA has been introduced inside the cell membrane. A number of transfection techniques are generally known in the art. See, e.g., Graham et al., Virology 52:456 (1973); Sambrook et al., Molecular Cloning: A Laboratory Manual (1989); Davis et al., Basic Methods in Molecular Biology (1986); Chu et al., Gene 13:197 (1981). Such techniques can be used to introduce one or more exogenous DNA moieties, such as a nucleotide integration vector and other nucleic acid molecules, into suitable host cells. The term captures chemical, electrical, and viral-mediated transfection procedures.

As used herein, "expression" refers to the process by which a nucleic acid is translated into peptides or is transcribed into RNA, which, for example, can be translated into peptides, polypeptides or proteins. If the nucleic acid is derived from genomic DNA, expression may, if an appropriate eukaryotic host cell or organism is selected, include splicing of the mRNA. For heterologous nucleic acid to be expressed in a host cell, it must initially be delivered into the cell and then, once in the cell, ultimately reside in the nucleus.

As used herein, "genetic therapy" involves the transfer of heterologous DNA to cells of a mammal, particularly a human, with a disorder or conditions for which therapy or diagnosis is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product; it may encode a product, such as a peptide or RNA that in some manner mediates, directly or indirectly, expression of a therapeutic product. Genetic therapy may also be used to deliver nucleic acid encoding a gene product to replace a defective gene or supplement a gene product produced by the mammal or the cell in which it is introduced. The introduced nucleic acid may encode a therapeutic compound, that is not normally produced in the mammalian host or that is not produced in therapeutically effective amounts or at a therapeutically useful time. The heterologous DNA encoding the therapeutic product may be modified prior to introduction into the cells of the afflicted host in order to enhance or otherwise alter the product or expression thereof.

As used herein, "heterologous nucleic acid sequence" is typically DNA that encodes RNA and proteins that are not normally produced in vivo by the cell in which it is expressed or that mediates or encodes mediators that alter expression of endogenous DNA by affecting transcription, translation, or other regulatable biochemical processes. A heterologous nucleic acid sequence may also be referred to as foreign DNA. Any DNA that one of skill in the art would recognize or consider as heterologous or foreign to the cell in which it is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

As used herein, the term "subject" or "patient" refers to animals into which the large DNA molecules can be introduced. Included are higher organisms, such as mammals and birds, including humans, primates, rodents, cattle, pigs, rabbits, goats, sheep, mice, rats, guinea pigs, cats, dogs, horses, chicken and others.

As used herein, "administering to a subject" is a procedure by which one or more delivery agents and/or large nucleic acid molecules, together or separately, are introduced into or applied onto a subject such that target cells which are present in the subject are eventually contacted with the agent and/or the large nucleic acid molecules.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrastemal injection and infusion.

The phrases "systemic administration," "administered systemically," "peripheral administration" and "administered peripherally" as used herein mean the administration of a compound, drug or other material other than directly into a target tissue (e.g., the left ventricular wall), such that it enters the animal's system and, thus, is subject to metabolism and other like processes, for example, subcutaneous administration.

As used herein, the term "cardiomyopathy" refers to the deterioration of the function of the myocardium (i.e., the actual heart muscle) for any reason. Subjects with cardiomyopathy are often at risk of arrhythmia or sudden cardiac death or both.

As used herein, the term "hypertrophic cardiomyopathy" refers to a disease of the heart and myocardium in which a portion of the myocardium is hypertrophied.

As used herein, the term "familial hypertrophic cardiomyopathy" refers to a genetic disorder characterized by increased growth (i.e., hypertrophy) in thickness of the wall of the left ventricle.

Embodiments described herein relate to methods and agents for the treatment of cardiomyopathies in a subject. The methods and agents described herein can directly target the cardiac myofilaments as a means to correct contractile dysfunction in the heart. It was found that expression of full-length wild-type cMyBPC by in vivo gene transfer in hypertrophic hearts deficient of wild-type or functional cMyBPC substantially improved systolic and diastolic contractile function, including fractional shortening, ejection fractions, and ejection times, and decreased left ventricular weights and end diastolic and systolic chamber dimensions. It was further found that full-length wild type cMyBPC can be modified by amino acid substitutions to generate agents capable of affecting contractile function in vivo and provided increased resistance to contractile damage due to ischemic injuries, long-term heart failure, end-stage heart failure, and/or atrial fibrillation. Therefore, embodiments described herein contemplate treating cardiomyopathies in a subject mediated by or resulting in, at least in part, cardio contraction dysfunction by administering to the subject an agent that causes or induces expression of cMyBPC, a mutant, variant, or fragment thereof, which can modulate contractile function in the myocardial tissue of the subject.

In some embodiments, the cardiomyopathies treated by the methods and agents can include but are not limited to cardiac diseases affiliated with mutations in cardiac myosin binding protein C (cMyBPC), such as hypertrophic cardiomyopathy and familial hypertophic cardiomyopathy (FHC). The cardiomyopathy treated by the methods and agents can also include cardiomyopathies associated with a pulmonary embolus, a venous thrombosis, a myocardial infarction, a transient ischemic attack, a peripheral vascular disorder, atherosclerosis, ischemic cardiac disease and/or other myocardial injury or vascular disease. In certain embodiments, the cardiomyopathies treated by the methods and agents described herein can include cardiac diseases associated with myocardial tissue hypercontractility, such as heart failure related to left ventricular hypercontractility.

In some embodiments, a method of treating a cardiomyopathy can include locally administering (or locally delivering) to weakened myocardial tissue, ischemic myocardial tissue, and/or hypertrophic myocardial tissue, an agent that causes or induces expression of cMyBPC or a mutant, variant, or fragment thereof to modulates contractile function of the myocardial tissue. In some embodiments, the amount, concentration, and volume of the agent that modulates contractile function in myocardial tissue administered to a subject can be controlled and/or optimized to substantially improve the functional parameters of the heart while mitigating adverse side effects. For example, the agent that modulates contractile function in a myocardial tissue can be administered directly or locally to a cMyBPC deficient myocardial tissue. A cMyBPC deficient myocardial tissue can include myocardial cells having a heterozygous or homozygous cMyBPC mutation.

In one example, the agent that modulates contractile function in a tissue can be administered directly or locally to a weakened region, ischemic region, and/or hypertrophic region of myocardial tissue of a mammal in which there is a deterioration or worsening of a parameter of the heart, such as left ventricular dimension or weight, or cardiac contractile function. In some aspects, the amount of the agent administered to the myocardial tissue, such as a weakened region, ischemic region, and/or hypertrophic region of the myocardial tissue of the mammal, can be an amount effective to improve at least one parameter of the myocardium including fractional shortening, ejection fraction, and ejection time, left ventricular weight, and end diastolic and systolic chamber dimensions.

The amount of the agent that modulates contractile function administered to myocardial tissue can also be an amount required to: increase expression of cMyBPC protein or a mutant, variant, or fragment thereof in the heart; preserve and/or improve contractile function; delay the emergence of hypertrophic cardiomyopathy or reverse the pathological course of the disease; increase myocyte viability; improve myofilament function; inhibit left ventricular hypertrophy; cardiac hypertrophy regression, normalize systolic and diastolic function in heart; and restore normal cross-bridge behavior at the myofilament level.

In some embodiments, an agent that induces cMyBPC expression or expression of a mutant, variant, or fragment thereof can include any agent that causes, increases, and/or upregulates expression of cMyBPC or a mutant, variant, or fragment thereof in a myocardial cell of the myocardium of the subject being treated. In certain embodiments, the cMyBPC that is expressed in the myocardial cells can include wild-type full length cMyBPC that has an amino acid sequence of SEQ ID NO: 1 or SEQ ID NO: 2.

In other embodiments, the agent that causes, increases, and/or upregulates expression of cMyBPC or a mutant, variant, or fragment thereof in myocardial tissue can include a nucleic acid that encodes wild-type cMyBPC or a mutant, variant, or fragment thereof, which modulate the contractile function of the myocardium. Nucleic acids that cause, increase, and/or upregulate expression of cMyBPC or variants thereof can include natural or synthetic cMyBPC nucleic acids that are incorporated into recombinant nucleic acid constructs, typically DNA constructs, capable of introduction into and replication in the cells of the myocardial tissue. Such a construct can include a replication system and sequences that are capable of transcription and translation of a polypeptide-encoding sequence in a given cell.

The cMyBPC nucleic acid that encodes the cMyBPC protein or a mutant, variant, or fragment thereof can be a native or non-native nucleic acid and be in the form of RNA or in the form of DNA (e.g., cDNA, genomic DNA, and synthetic DNA). The DNA can be double-stranded or single-stranded, and if single-stranded may be the coding (sense) strand or non-coding (anti-sense) strand. The nucleic acid coding sequence that encodes cMyBPC may be substantially similar to a nucleotide sequence of the cMyBPC gene. For examples, nucleic acids that encode wild-type cMyBPC can have a nucleotide sequence of SEQ ID NO: 3 or SEQ ID NO: 4.

Other nucleic acid molecules that encode cMyBPC or a mutant, variant, or fragment thereof can include those that encode fragments, analogs and derivatives of native cMyBPC. Such variants may be, for example, a naturally occurring allelic variant of a native cMyBPC gene, a homolog or ortholog of a native cMyBPC gene, or a non-naturally occurring variant of a native cMyBPC gene. These variants have a nucleotide sequence that differs from a native cMyBPC gene in one or more bases. For example, the nucleotide sequence of such variants can feature a deletion, addition, or substitution of one or more nucleotides of a native cMyBPC gene. Nucleic acid insertions are preferably of about 1 to 10 contiguous nucleotides, and deletions are preferably of about 1 to 10 contiguous nucleotides.

A cMyBPC variant can include polynucleotides that encode proteins that constitutively express the functional activities of native cMyBPC. Other cMyBPC variants can include those that encode polypeptides that are resistant to proteolytic cleavage, as for example, due to mutations, which alter protease target sequences. Whether a change in the amino acid sequence of a peptide results in a variant having one or more functional activities of a native cMyBPC can be readily determined by testing the variant for a native cMyBPC functional activity.

In other applications, variant cMyBPC displaying substantial changes in structure can be generated by making nucleotide substitutions that cause less than conservative changes in the encoded polypeptide. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue (e.g., serine or threonine), for (or by) a hydrophobic residue (e.g., leucine, isoleucine, phenylalanine, valine or alanine); (b) a cysteine or proline for (or by) any other residue; (c) a residue having an electropositive side chain (e.g., lysine, arginine, or histidine), for (or by) an electronegative residue (e.g., glutamine or aspartic acid); or (d) a residue having a bulky side chain (e.g., phenylalanine), for (or by) one not having a side chain, (e.g., glycine).

Naturally occurring allelic variants of a native cMyBPC gene are nucleic acids isolated from mammalian tissue that have at least 70% sequence identity with a native cMyBPC gene, and encode polypeptides having structural similarity to a native cMyBPC polypeptide. Homologs of a native cMyBPC gene are nucleic acids isolated from other species that have at least 70% sequence identity with the native gene, and encode polypeptides having structural similarity to a native cMyBPC polypeptide. Public and/or proprietary nucleic acid databases can be searched to identify other nucleic acid molecules having a high percent (e.g., 70% or more) sequence identity to a native cMyBPC gene.

Non-naturally occurring cMyBPC gene variants are nucleic acids that do not occur in nature (e.g., are made by the hand of man), have at least 70% sequence identity with a native cMyBPC gene, and encode polypeptides having structural similarity to a native cMyBPC polypeptide. Examples of non-naturally occurring cMyBPC gene variants are those that encode a fragment of a native cMyBPC protein, those that hybridize to a native cMyBPC gene or a complement to a native cMyBPC gene under stringent conditions, and those that share at least 65% sequence identity with a native cMyBPC gene or a complement of a native cMyBPC gene.

In some embodiments, the agent can include a nucleic acid that can be used to express a variant cMyBPC protein, which has a triple S to D mutation. The variant cMyBPC protein, which has a triple S to D mutation, when expressed in myocardial tissue can increase contractile function of the myocardium. The S to D phosphorylation mutation can be S273D, S282D, and S302D for SEQ ID NO: 1 and S275D, S284D, and S304D for SEQ ID NO: 2. The variant cMyBPC proteins expressed with the S to D mutation can have an amino acid sequence of SEQ ID NO: 5 or SEQ ID NO: 6.

In other embodiments, the agent can comprise a nucleic acid that can be used to express a variant cMyBPC protein, which includes a triple S to A mutation. The variant cMyBPC protein, which has a triple S to A mutation, when expressed in myocardial tissue can decrease contractile function of the myocardium. The S to A mutation can be S273A, S282A, and S302A for SEQ ID NO: 1 and S275A, S284A, and S304A for SEQ ID NO: 2. The variant cMyBPC proteins expressed with the S to A mutation can have an amino acid sequence of SEQ ID NO: 7 or SEQ ID NO: 8.

In still other embodiments, the agent can include a nucleic acid that can be used to express a fragment of cMyBPC protein that includes or consists of the C0-C2 domains of wild-type cMyBPC or variant cMyBPC.

Nucleic acids that hybridize under stringent conditions to one of the foregoing nucleic acids can also be used. For example, such nucleic acids can be those that hybridize to one of the foregoing nucleic acids under low stringency conditions, moderate stringency conditions, or high stringency conditions.

Nucleic acid molecules encoding a cMyBPC fusion protein may also be used. Such nucleic acids can be made by preparing a construct (e.g., an expression vector) that expresses a cMyBPC fusion protein when introduced into a target cell. For example, such a construct can be made by ligating a first polynucleotide encoding a cMyBPC protein fused in frame with a second polynucleotide encoding another protein such that expression of the construct in a suitable expression system yields a fusion protein.

The nucleic acids encoding cMyBPC or a mutant, variant, or fragment thereof can be modified at the base moiety, sugar moiety, or phosphate backbone, for example, to improve stability of the molecule, hybridization, etc. The nucleic acids within the invention may additionally include other appended groups such as peptides (e.g., for targeting target cell receptors in vivo), or agents facilitating transport across the cell membrane, hybridization-triggered cleavage. To this end, the nucleic acids may be conjugated to another molecule, (e.g., a peptide) hybridization triggered cross-linking agent, transport agent, hybridization-triggered cleavage agent, etc.

One method of introducing the agent into a target cell involves using gene therapy. Gene therapy as described herein can be used to induce cMyBPC expression in a myocardial cell in vivo.

In some embodiments, the gene therapy can use a vector including a nucleic acid encoding a cMyBPC protein or a variant thereof. A "vector" (sometimes referred to as gene delivery or gene transfer "vehicle") refers to a macromolecule or complex of molecules comprising nucleic acids to be delivered to a target cell, either in vitro or in vivo. The nucleic acids to be delivered may comprise a coding sequence of interest in gene therapy. Vectors include, for example, viral vectors (such as adenoviruses ('Ad'), adeno-associated viruses (AAV), and retroviruses), non-viral vectors, liposomes, and other lipid-containing complexes, and other macromolecular complexes capable of mediating delivery of a polynucleotide to a target cell.

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities.

Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e. positive/negative) markers (see, e.g., Lupton, S., WO 92/08796, published May 29, 1992; and Lupton, S., WO 94/28143, published Dec. 8, 1994). Such marker genes can provide an added measure of control that can be advantageous in gene therapy contexts. A large variety of such vectors are known in the art and are generally available.

Vectors for use in the methods described herein include viral vectors, lipid based vectors and other non-viral vectors that are capable of delivering a nucleotide to the cells of myocardial tissue. The vector can be a targeted vector, for example, a targeted vector that preferentially binds to the cells of weakened region, ischemic region, and/or hypertrophic region of the myocardial tissue. Viral vectors can include those that exhibit low toxicity to the cells of the myocardial and vascular tissue and induce production of therapeutically useful quantities of cMyBPC protein or a mutant, variant, or fragment thereof in a tissue-specific manner.

Examples of viral vectors are those derived from adenovirus (Ad) or adeno associated virus (AAV). Both human and non-human viral vectors can be used and the recombinant viral vector can be replication-defective in humans. Where the vector is an adenovirus, the vector can comprise a polynucleotide having a promoter operably linked to a gene encoding the cMyBPC protein and is replication-defective in humans.

Other viral vectors that can be used include herpes simplex virus (HSV)-based vectors. HSV vectors deleted of one or more immediate early genes (IE) are advantageous because they are generally non-cytotoxic, persist in a state similar to latency in the target cell, and afford efficient target cell transduction. Recombinant HSV vectors can incorporate approximately 30 kb of heterologous nucleic acid.

Retroviruses, such as C-type retroviruses and lentiviruses, might also be used in the invention. For example, retroviral vectors may be based on murine leukemia virus (MLV). See, e.g., Hu and Pathak, Pharmacol. Rev. 52:493-511, (2000) and Fong et al., Crit. Rev. Ther. Drug Carrier Syst. 17:1-60, (2000). MLV-based vectors may contain up to 8 kb of heterologous (therapeutic) DNA in place of the viral genes. The heterologous DNA may include a tissue-specific promoter and a cMyBPC nucleic acid. In methods of delivery to cells proximate the wound, it may also encode a ligand to a tissue specific receptor.

Additional retroviral vectors that might be used are replication-defective lentivirus-based vectors, including human immunodeficiency (HIV)-based vectors. See, e.g., Vigna and Naldini, J. Gene Med. 5:308-316, 2000 and Miyoshi et al., J. Virol. 72:8150-8157, 1998. Lentiviral vectors are advantageous in that they are capable of infecting both actively dividing and non-dividing cells. They are also highly efficient at transducing human epithelial cells.

Lentiviral vectors for use in the invention may be derived from human and non-human (including SIV) lentiviruses. Examples of lentiviral vectors include nucleic acid sequences required for vector propagation as well as a tissue-specific promoter operably linked to a cMyBPC gene or variant thereof. These former may include the viral LTRs, a primer binding site, a polypurine tract, att sites, and an encapsidation site.

A lentiviral vector may be packaged into any suitable lentiviral capsid. The substitution of one particle protein with another from a different virus is referred to as "pseudotyping". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

In one particular embodiment, stable transfection of a target cell is accomplished using a recombinant lentiviral vector encoding the wild-type full length cMyBPC (e.g., SEQ ID NO: 3 or SEQ ID NO: 4) and a CMV promoter (see Example below). Lentiviral vector constructs can further include other genes involved in inherited HCM, such as myosin heavy chain (MHC).

Alphavirus-based vectors, such as those made from semliki forest virus (SFV) and sindbis virus (SIN) might also be used in the invention. Use of alphaviruses is described in Lundstrom, K., Intervirology 43:247-257, (2000) and Perri et al., Journal of Virology 74:9802-9807, (2000).

Recombinant, replication-defective alphavirus vectors are advantageous because they are capable of high-level heterologous (therapeutic) gene expression, and can infect a wide target cell range. Alphavirus replicons may be targeted to specific cell types by displaying on their virion surface a functional heterologous ligand or binding domain that would allow selective binding to target cells expressing a cognate binding partner. Alphavirus replicons may establish latency, and therefore long-term heterologous nucleic acid expression in a target cell. The replicons may also exhibit transient heterologous nucleic acid expression in the target cell.

In many of the viral vectors compatible with methods described herein, more than one promoter can be included in the vector to allow more than one heterologous gene to be expressed by the vector. Further, the vector can comprise a sequence, which encodes a signal peptide or other moiety which facilitates the expression of a cMyBPC gene product from the target cell.

To combine advantageous properties of two viral vector systems, hybrid viral vectors may be used to deliver a cMyBPC nucleic acid described above to a target tissue. Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral ITRs may be used to transduce cells. In another variation, an AAV vector may be placed into a "gutless", "helper-dependent" or "high-capacity" adenoviral vector. Adenovirus/AAV hybrid vectors are discussed in Lieber et al., J. Virol. 73:9314-9324, (1999). Retrovirus/adenovirus hybrid vectors are discussed in Zheng et al., Nature Biotechnol. 18:176-186, (2000). Retroviral genomes contained within an adenovirus may integrate within the target cell genome and effect stable cMyBPC gene expression.

Other nucleotide sequence elements which facilitate expression of the cMyBPC gene and cloning of the vector are further contemplated. For example, the presence of enhancers upstream of the promoter or terminators downstream of the coding region, for example, can facilitate expression.

In some embodiments, a tissue-specific promoter can be fused to a cMyBPC encoding nucleic acid. By fusing such tissue specific promoter within a vector construct, transgene expression is limited to a particular tissue. The efficacy of gene expression and degree of specificity provided by tissue specific promoters can be determined, using the recombinant adenoviral system of the present invention. In an exemplary embodiment, a nucleic acid encoding a cMyBPC mutant protein can be expressed in myocytes using a lentiviral or recombinant adeno-associated virus (rAAV)-mediated gene delivery under the control of the cardiac troponin I promoter as disclosed in US Pat. Appln. No. 2009/0325170A1 to Pinto et al.

In addition to viral vector-based methods, non-viral methods may also be used to introduce a cMyBPC nucleic acid into a target cell. A review of non-viral methods of gene delivery is provided in Nishikawa and Huang, Human Gene Ther. 12:861-870, (2001). An example of a non-viral gene delivery method according to the invention employs plasmid DNA to introduce a cMyBPC nucleic acid into a cell. Plasmid-based gene delivery methods are generally known in the art.

Optionally, a synthetic gene transfer molecule can be designed to form multimolecular aggregates with plasmid cMyBPC DNA. These aggregates can be designed to bind to cells of weakened region, ischemic region, and/or peri-infarct region of the myocardial tissue. Cationic amphiphiles, including lipopolyamines and cationic lipids, may be used to provide receptor-independent cMyBPC nucleic acid transfer into target cells (e.g., cardiomyocytes). In addition, preformed cationic liposomes or cationic lipids may be mixed with plasmid DNA to generate cell-transfecting complexes. Methods involving cationic lipid formulations are reviewed in Feigner et al., Ann N.Y. Acad. Sci. 772:126-139, (1995) and Lasic and Templeton, Adv. Drug Delivery Rev. 20:221-266, 1996. For gene delivery, DNA may also be coupled to an amphipathic cationic peptide (Fominaya et al., J. Gene Med. 2:455-464, (2000)).

Methods that involve both viral and non-viral based components may be used according to the invention. For example, an Epstein Barr virus (EBV)-based plasmid for therapeutic gene delivery is described in Cui et al., Gene Therapy 8:1508-1513, (2001). Additionally, a method involving a DNA/ligand/polycationic adjunct coupled to an adenovirus is described in Curiel, D. T., Nat. Immun. 13:141-164, 1994.

Additionally, the cMyBPC nucleic acid can be introduced into the target cell by transfecting the target cells using electroporation techniques. Electroporation techniques are well known and can be used to facilitate transfection of cells using plasmid DNA.

Vectors that encode the expression of cMyBPC or a variant thereof can be delivered to the target cell in the form of an injectable preparation containing pharmaceutically acceptable carrier, such as saline, as necessary. Other pharmaceutical carriers, formulations and dosages can also be used in accordance with the present invention.

It will be appreciated that the amount, volume, concentration, and/or dosage of cMyBPC vector that is administered to any one animal or human depends on many factors, including the subject's size, body surface area, age, the particular composition to be administered, sex, time and route of administration, general health, and other drugs being administered concurrently. Specific variations of the above noted amounts, volumes, concentrations, and/or dosages of cMyBPC vector can be readily be determined by one skilled in the art using the experimental methods described below. In one exemplary embodiment described below, a therapeutically effective amount is 20-25 µl of a lentiviral cMyBPC vector ($1 \times 10^9$ CFU/ml).

Where the target cell comprises a cell within or proximate a myocardial tissue being treated, the vector can be delivered by direct injection at an amount sufficient for the cMyBPC to be expressed to a degree which allows for highly effective therapy. By injecting the vector directly into or about the periphery of the target tissue, it is possible to target the vector transfection rather effectively, and to minimize loss of the recombinant vectors. This type of injection enables local transfection of a desired number of cells, especially about the injury, thereby maximizing therapeutic efficacy of gene transfer, and minimizing the possibility of an inflammatory response to viral proteins.

The cMyBPC vector can also be administered by direct injection using endo-ventricular catheterization. In one example, a deflectable guide catheter device can be advanced to a left ventricle retrograde across the aortic valve. Once the device is positioned in the left ventricle, cMyBPC vector can be injected into the peri-infarct region (both septal and posterolateral aspect) area of the left ventricle.

cMyBPC or variants thereof can be expressed for any suitable length of time within the cells of the target tissue, including transient expression and stable, long-term expression. In one aspect of the invention, the cMyBPC nucleic acid will be expressed in therapeutic amounts for a defined length of time effective to modulate contractile function in a myocardial tissue of the subject.

In some embodiments, the myocardial tissue of the subject can be imaged prior to administration of the cMyBPC vector to define the target area prior to administration of the cMyBPC vector. Defining the weakened, ischemic, and/or hypertrophic region or a region that is deficient in cMyBPC allows for more accurate intervention and targeting of the cMyBPC vector to the targeted region. The imaging technique used to define the targeted region of the myocardial tissue or vascular tissue can include any known imaging technique. Such imaging techniques can include, for example, at least one of echocardiography, magnetic resonance imaging, coronary angiogram, electroanatomical mapping, or fluoroscopy. It will be appreciated that other imaging techniques that can define the targeted region can also be used. In some embodiments, a subject's target tissue can be evaluated at about 21 days following administration of an agent described herein as determined by an in vivo echocardiography contractile function analysis, such as transthoracic echocardiography or using a cMyBPC specific antibody.

Optionally, other agents besides cMyBPC nucleic acids (e.g., cMyBPC vectors) can be introduced into cells of the myocardial to promote expression of cMyBPC in the cells of the target region. For example, agents that increase the transcription of a gene encoding cMyBPC increase the translation of an mRNA encoding cMyBPC, and/or those that decrease the degradation of an mRNA encoding cMyBPC could be used to increase cMyBPC protein levels. Increasing the rate of transcription from a gene within a cell can be accomplished by introducing an exogenous promoter upstream of the gene encoding cMyBPC. Enhancer elements, which facilitate expression of a heterologous gene, may also be employed.

In some embodiments, an agent that modulates contractile function in a myocardial tissue can include a cMyBPC peptide fragment that is delivered to a subject by administering a shortened cMyBPC peptide to cells of myocardial or vascular tissue. In some aspects, the agent is a small molecule. Exemplary agents can include one or more peptides having substantial similarity with cMyBPC peptide functional domains, such a peptide including the C0-C2 domains. For example, a cMyBPC peptide fragment can include a peptide having substantial similarity with at least one of a cMyBPC PA (proline-alanine) domain, a cMyBPC C1 domain, and a cMyBPC triple phosphorylation mutant domain. The triple phosphorylation mutant domain can include a triple S to D phosphorylation mutant domain. Alternatively, the triple phosphorylation mutant domain can include a triple S to A phosphorylation mutant domain.

The agents described herein, which modulates contractile function in a myocardial tissue, can be administered to the myocardial or vascular tissue neat or in a pharmaceutical composition. The pharmaceutical composition can provide localized release of an agent described herein to the cells of the target region being treated. Pharmaceutical compositions in accordance with the invention will generally include an amount of an agent admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. Moreover, for human administration, preparations should meet sterility, pyrogenicity, general safety and purity standards as required by FDA Office of Biological Standards.

The pharmaceutical composition can be in a unit dosage injectable form (e.g., solution, suspension, and/or emulsion). Examples of pharmaceutical formulations that can be used for injection include sterile aqueous solutions or dispersions and sterile powders for reconstitution into sterile injectable solutions or dispersions. The carrier can be a solvent or dispersing medium containing, for example, water, ethanol, polyol (e.g., glycerol, propylene glycol, liquid polyethylene glycol, and the like), dextrose, saline, or phosphate-buffered saline, suitable mixtures thereof and vegetable oils.

Proper fluidity can be maintained, for example, by the use of a coating, such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions.

Additionally, various additives, which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various amounts of the other ingredients, as desired.

Pharmaceutical "slow release" capsules or "sustained release" compositions or preparations may be used and are generally applicable. Slow release formulations are generally designed to give a constant drug level over an extended period and may be used to deliver the agent. The slow release formulations are typically implanted in the vicinity of the target tissue, for example, the vicinity of weakened, ischemic, and/or peri-infarct region of myocardial tissue.

Examples of sustained-release preparations include semipermeable matrices of solid hydrophobic polymers containing the agent, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919; copolymers of L-glutamic acid and γ ethyl-L-glutamate; non-degradable ethylene-vinyl acetate; degradable lactic acid-glycolic acid copolymers, such as the LUPRON DEPOT (injectable microspheres composed of lactic acid-glycolic acid copolymer and leuprolide acetate); and poly-D-(−)-3-hydroxybutyric acid.

While polymers, such as ethylene-vinyl acetate and lactic acid-glycolic acid enable release of molecules for over 100 days, certain hydrogels release proteins for shorter time periods. When encapsulated, the agent can remain in the body for a long time, and may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thio-disulfide interchange, stabilization is achieved by modifying sulfhydryl residues, lyophilizing from acidic solutions, controlling moisture content, using appropriate additives, developing specific polymer matrix compositions, and the like.

In certain embodiments, liposomes and/or nanoparticles may also be employed with the agent. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios, the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

For preparing pharmaceutical compositions from the compounds described herein, pharmaceutically acceptable carriers can be in any suitable form (e.g., solids, liquids, gels, etc.). A solid carrier can be one or more substances, which may also act as diluents, flavoring agents, binders, preservatives, and/or an encapsulating material.

In another embodiment, an agent described herein can also be provided in or on a surface of a medical device used to treat a myocardial or vascular tissue. The medical device can comprise any instrument, implement, machine, contrivance, implant, or other similar or related article, including a component or part, or accessory, which is, for example, recognized in the official U.S. National Formulary, the U.S. Pharmacopoeia, or any supplement thereof; is intended for use in the diagnosis of disease or other conditions, or in the cure, mitigation, treatment, or prevention of disease, in humans or in other animals; or, is intended to affect the structure or any function of the body of humans or other animals, and which does not achieve any of its primary intended purposes through chemical action within or on the body of man or other animals, and which is not dependent upon being metabolized for the achievement of any of its primary intended purposes.

The medical device can include, for example, endovascular medical devices, such as intracoronary medical devices. Examples of intracoronary medical devices can include stents, drug delivery catheters, grafts, and drug delivery balloons utilized in the vasculature of a subject. Where the medical device comprises a stent, the stent may include peripheral stents, peripheral coronary stents, degradable coronary stents, non-degradable coronary stents, self-expanding stents, balloon-expanded stents, and esophageal stents. The medical device may also include arterio-venous grafts, by-pass grafts, vascular implants and grafts, intravenous catheters, small diameter grafts, artificial lung catheters, electrophysiology catheters, bone pins, suture anchors, blood pressure and stent graft catheters, implanted drug infusion tubes, neurological catheters, central venous access catheters, catheter cuff, vascular access catheters, urological catheters/implants, atherectomy catheters, clot extraction catheters, PTA catheters, PTCA catheters, stylets (vascular and non-vascular), drug infusion catheters, angiographic catheters, hemodialysis catheters, neurovascular balloon catheters, thoracic cavity suction drainage catheters, electrophysiology catheters, stroke therapy catheters, abscess drainage catheters, dialysis catheters, and central venous access catheters.

The medical device may additionally include either implantable pacemakers or defibrillators, vascular grafts, hemostatic barriers, clamps, surgical staples/sutures/screws/plates/wires/clips, glucose sensors, blood oxygenator tubing, blood oxygenator membranes, blood bags, wound dressings, embolic protection filters, abdominal aortic aneurysm grafts and devices, neuroaneurysm treatment coils, hemodialysis devices, anastomotic closures, aneurysm exclusion devices, neuropatches, vena cava filters, endoscopic surgical and wound drainings, surgical tissue extractors, transition sheaths and dialators, coronary and peripheral guidewires, circulatory support systems, percutaneous closure devices, vascular coils, vascular protection devices, vascular intervention devices including vascular filters and distal support devices and emboli filter/entrapment aids, AV access grafts, surgical tampons, cardiac valves, and tissue engineered constructs, such as bone grafts and skin grafts.

The following examples are for the purpose of illustration only and are not intended to limit the scope of the claims, which are appended hereto.

Example 1

This Example demonstrates that increasing the levels of cMyBPC in the intact heart can improve contractile function of hearts deficient in cMyBPC. The expression levels of cMyBPC in cMyBPC$^{-/-}$ hearts were increased by transfecting the myocardium in vivo with recombinant viral vectors to restore levels of cMyBPC in the sarcomere and reverse abnormal cross-bridge behavior at the myofilament level. We also found that increasing the expression level of cMyBPC in hearts restored cross-bridge function and improved impaired contractile function in vivo. This Example establishes the feasibility of cMyBPC gene therapy in a mouse model of FHC, and provides a platform for the clinical application of cMyBPC gene therapy for treatment of cMyBPC related FHC.

Detailed Methods
Preparation and Purification of Recombinant Lentivirus Vectors

A 3.8 kilobase cDNA fragment encoding the complete cDNA copy of murine cMyBPC was cloned from a recombinant vector pET 28b (Promega) using PCR TOPO cloning kit (pCR 8/GW/TOPO TA Cloning Kit, K2500-20SC, Invitrogen) in accordance with the manufacturer's instructions. The forward primer sequence was 5'-atgccggagc cagggaagaa accag-3'(SEQ ID NO: 9) and the reverse primer sequence was 5'-tcactgaggaactcgcacctccag-3' (SEQ ID NO: 10). To construct the recombinant lentivirus (LcMyBPC) we used a lentivirus preparation kit from Invitrogen (Catalogue no. K4934-00). The cMyBPC cDNA and CMV promoter were cloned into the lentivirus destination vector pLenti6.4/R4R2/V5-DEST using the Gateway approach according to the protocol provided by Invitrogen. Briefly, three plasmids CMV/topo, cMyBPC/topo and pLenti6.4 were mixed in one tube following addition of LR recombinase. After 16 hours incubation at room temperature the reaction mix was used for transformation of Stb13 E. coli competent cells (Invitrogen). Selected clones were propagated and plasmid DNA was purified using a QIAgen kit and analyzed by digestion and sequencing. A lentivirus destination vector containing a CMV promoter and cMyBPC cDNA was propagated and DNA purified by MAXI Endotoxin free Kit (QIAgen).

Lentivirus particles were produced by co-transfection of 293T cells with the destination vector pLenti6.4/R4R2/V5-DEST containing cMyBPC cDNA driven by CMV promoter and Viral Power Plasmid Mix (Invitrogen) using Lipofectamine 2000 as the transfecting agent. Briefly, 9 µg of Viral Power Mix and 4 µg DEST vector were mixed in a tube containing 1.5 mL of Opti-MEM reduced serum media and 40 µl Lipofectamine 2000 were added to another tube containing 1.5 mL of Opti-MEM reduced serum media. The contents of both tubes were combined and incubated for 20 minutes at room temperature. Then Lipofectamine-DNA complexes were added to 293T cells on tissue culture plates and incubated overnight in a 95% $O_2$ and 5% $CO_2$ environment at 37° C. The following morning Lipofectamine containing medium was replaced with complete 293T medium (DMEM, 10% FBS, 1% P/S). Twenty four hours later medium containing virus particles was collected and virus particles were isolated by filtering the medium through 0.45 µm syringe filter (Millipore Millex-HV low protein binding Durapore (PVDF) (Catalogue no. SLHY033RS) attached to a 60 ml syringe. 30 ml aliquots of virus particles were added to 2 ml of 20% sucrose solution in 38.5 ml centrifuge tubes (Beckman, #355642), and unitracentrefuged at 25000 rpm for 2.5 hours at 4° C., using a SW28 rotor. The resulting pellet was resuspended in 60 µl cold HBSS (Invitrogen #14025), aliquoted in eppendorff tubes and stored at −80° C. until use. Virus titter was determined by a Lenti-GOStix kit (Clontech) and SYBR-based qRT-PCR kit (ABM, LV900) according to the manufactures' instructions using an Applied Biosystems RT-PCR platform.

Myocardial In Vivo cMyBPC Gene Transfer

Adult male cMyBPC$^{-/-1}$ and wild-type (WT) mice of the SV/129 strain (8-26 weeks of age) were used in this study. Mice were anesthetized with 1-2% isoflurane, intubated and placed on artificial ventilation (80-100 breaths/minute). A thoracotomy was performed over the third intercostals space of the left thorax to expose the heart. A syringe with a 30 gauge fine needle was inserted into the LV free wall in between the muscle layers of the LV approximately equidistant from the apical tip and the mid-LV. The tip of the needle was oriented almost parallel to the apex-base plane of the LV and at ~50% wall depth in between the epicardial and endocardial layers of the myocardium. The tip of the needle was carefully advanced beyond the mid-LV towards the LV base and 20-25 µl of lentivirus was slowly released into the myocardium ($2 \times 10^9$ CFU/ml) as the syringe was slowly regressed towards the apex. After virus injection the syringe was withdrawn the chest was closed and negative pleural pressure reestablished before extubation. All procedures involving animal care and handling were performed according to institutional guidelines set forth by the Animal Care and Use Committee at Case Western Reserve University.

Expression and Purification of Recombinant cMyBPC

Purified recombinant cMyBP-C was generated as previously described. The full length mouse cMyBP-C DNA sequence containing an 11-amino acid N-terminal FLAG-tag epitope were cloned into tpFastB acl plasmids (Invitrogen) and used for transposition of expression cassettes into bacmids. Baculovirus strains were prepared according to the manufacturer's instructions, and were used to infect Sf9 cell monolayers. Cells were collected 80-96 h after infection, and recombinant cMyBP-C was extracted and purified on anti-FLAG M2 agarose columns (Sigma).

In Vitro Mechanical Experiments and In Vivo Assessment of Contractile Function

Mechanical measurements on skinned multicellular ventricular myocardium isolated from cMyBPC$^{-/-}$ hearts 21 days and 20 weeks following gene transfer (cMyBPC or vehicle) were performed. Mechanical measurements were also performed on cMyBPC$^{-/-}$ skinned myocardium following reconstitution with recombinant cMyBPC to directly compare the effects of increased cMyBPC expression by in vitro and in vivo techniques. To assess the effects of cMyBPC gene transfer on in vivo cardiac contractile function and morphology, transthoracic echocardiography was performed on a separate group of cMyBPC$^{-/-}$ mice 21 days following cMyBPC gene transfer (cMyBPC or vehicle).

Myofibrillar Protein Content and RNA Analysis

The cMyBPC content was measured in individual skinned myocardial preparations used for mechanical experiments by SDS-PAGE and western blotting. Tissue homogenates were also prepared from ventricular preparations isolated from WT, cMyBPC$^{-/-}$, and cMyBPC$^{-/-}$ mice following cMyBPC gene transfer, for analysis of myofibrillar protein content and phosphorylation by SDS-PAGE and western blotting. The content of cMyBPC was also evaluated in ventricular homogenates isolated from hearts that underwent echocardiographic studies following cMyBPC gene transfer. Expression levels of hypertrophic marker genes following cMyBPC gene transfer were evaluated by reverse transcription PCR.

Fluorescence Imaging Immunohistochemistry

Immunofluorescent detection of cMyBPC was performed by confocal microscopy on skinned myocardium and whole heart sections isolated from WT, cMyBPC$^{-/-}$, and virus treated cMyBPC$^{-/-}$ mice 21 days post gene transfer.

Statistical Analysis

Skinned fiber mechanical data were analyzed as previously described. Comparisons of in vitro and in vivo measurements between groups were performed using a one-way analysis of variance (ANOVA) with Tukey post-hoc test. Statistical significance was defined as P<0.05.

Results

Figure 5:
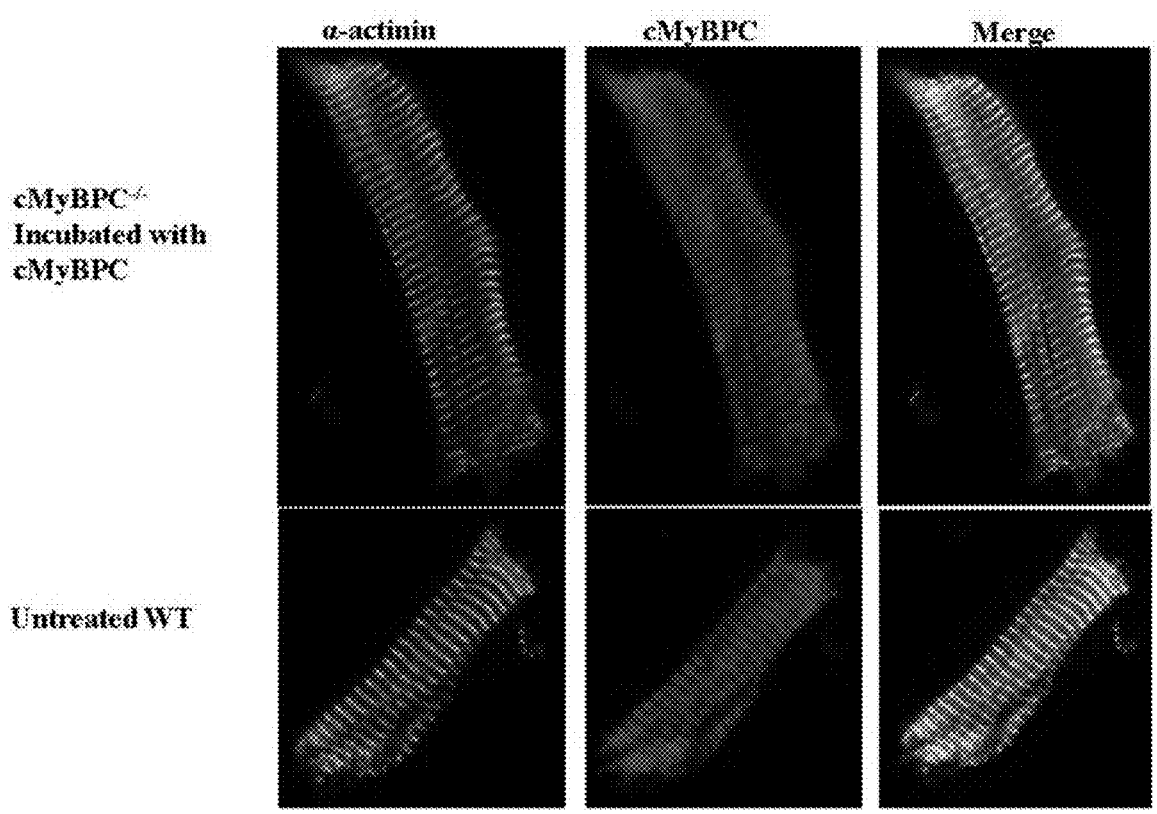
FIG. 5 illustrates confocal images (40× magnification) showing the localization of α-actinin (green) and cMyBPC (red) within the sarcomere for cMyBPC$^{-/-}$ skinned fibers following incubation with recombinant full-length mouse cMyBPC protein, and untreated WT skinned fibers.

Myofilament Protein Expression and Phosphorylation in WT and cMyBPC$^{-/-}$ Virus Treated Myocardium Used for In Vitro Mechanical Studies The cMyBPC content of individual fibers isolated from LcMyBPC treated cMyBPC$^{-/-}$ LV that were used for mechanical experiments was not different than the cMyBPC content of fibers isolated from WT LV, or cMyBPC$^{-/-}$ fibers following in vitro reconstitution using recombinant cMyBPC (Table 1). In contrast, no cMyBPC expression was detected in skinned myocardium isolated from vehicle-treated cMyBPC$^{-/-}$ LV (i.e., LCMV) (FIGS. 1-3). The sarcomeric localization of cMyBPC in skinned myocardium isolated from LcMyBPC-treated cMyBPC$^{-/-}$ hearts and cMyBPC$^{-/-}$ myocardium reconstituted with cMyBPC was probed by immunohistochemistry and showed similar staining patterns to WT myocardium suggesting that in vivo and in vitro cMyBPC reconstitution resulted in proper cMyBPC incorporation within the sarcomere (FIGS. 4-5). Myofilament protein expression and phosphorylation was assessed in myocardium isolated from the region of the viral injection site (mid-LV to apex) of WT, cMyBPC$^{-/-}$, and virus-treated cMyBPC$^{-/-}$ hearts that were used for mechanical experiments. No significant differences in the relative abundance or phosphorylation status of myofilament proteins was detected between groups (FIGS. 1-3). As expected, cMyBPC was not detected in fibers isolated from untreated and vehicle-treated cMyBPC$^{-/-}$ hearts, however, fibers isolated from LcMyBPC-treated cMyBPC$^{-/-}$ hearts (21 days following cMyBPC gene transfer) expressed cMyBPC at a level of 97±7% of the cMyBPC content of fibers isolated from WT hearts. Expression of cMyBPC in LcMyBPC-treated hearts was stable and was maintained at a high level (87±12% of the cMyBPC content of WT fibers) 20 weeks post gene transfer (Table 1). Expression of βMHC was slightly elevated in skinned myocardium isolated from untreated cMyBPC$^{-/-}$ hearts (16±5%, P<0.05) compared to WT myocardium, and was nearly absent in myocardium isolated from LcMyBPC treated cMyBPC$^{-/-}$ hearts (4±3%, NS) (FIGS. 1-3).

TABLE 1

Steady state and dynamic mechanical properties of skinned fibers isolated from WT and cMyBPC$^{-/-}$ hearts, following viral treatment and in vitro cMyBPC reconstructions

| | Total cMyBPC Content (%) | Fmin (mN/mm$^2$) | Fmax (mN/mm$^2$) | pCa$_{50}$ | n$_H$ |
|---|---|---|---|---|---|
| WT (5) | 100 ± 2 | 0.67 ± 0.10 | 19.35 ± 1.22 | 5.78 ± 0.01 | 4.51 ± 0.36 |
| cMyBPC$^{-/-}$ (4) | 0 ± 0* | 0.49 ± 0.13 | 20.36 ± 1.43 | 5.81 ± 0.01 | 4.20 ± 0.49 |
| cMyBPC$^{-/-}$ + LCMV (3) | 0 ± 0* | 0.56 ± 0.18 | 19.25 ± 1.75 | 5.79 ± 0.02 | 4.18 ± 0.61 |
| cMyBPC$^{-/-}$ + LcMyBPC (21 days) (5) | 97 ± 7 | 0.63 ± 0.12 | 20.67 ± 1.19 | 5.81 ± 0.02 | 4.29 ± 0.42 |
| cMyBPC$^{-/-}$ + LcMyBPC (20 weeks) (3) | 87 ± 12 | 0.64 ± 0.23 | 19.57 ± 2.02 | 5.79 ± 0.02 | 4.40 ± 0.62 |
| cMyBPC$^{-/-}$ + cMyBPC (5) | 98 ± 9 | 0.69 ± 0.22 | 21.08 ± 2.17 | 5.79 ± 0.02 | 4.27 ± 0.44 |

Data are means ± SE. Skinned ventricular fibers (20-25/group) was isolated from 3-5 mice per/group (indicated in parenthesis). All data presented for each sub-group was collected from the number of mice indicated in the left column. Total cMyBPC (%), percent cMyBPC content in individual fibers, Fmin, Ca$^{2+}$-independent force at pCa 9.0; Fmax, maximal Ca$^{2+}$-activated force at pCa 4.5; pCa$_{50}$, pCa required for half-maximal force generation; n$_H$, Hill-coefficient for force-pCa relationship. cMyBPC$^{-/-}$ + LCMV; vehicle-treated cMyBPC$^{-/-}$, cMyBPC$^{-/-}$ + LcMyBPC; LcMyBPC-treated cMyBPC$^{-/-}$ 21 days or 20 weeks following gene transfer, cMyBPC$^{-/-}$ + cMyBPC; in vitro reconstitution of cMyBPC$^{-/-}$ myocardium with recombinant cMyBPC.
*Significantly different from WT, P < 0.001.

Mechanical Properties of Skinned Myocardium Isolated from cMyBPC$^{-/-}$ Hearts Following In Vivo cMyBPC Gene Transfer and Reconstitution with Recombinant cMyBPC The steady-state mechanical properties of skinned myocardium isolated from WT, cMyBPC$^{-/-}$, LcMyBPC treated cMyBPC$^{-/-}$ hearts (21 days and 20 weeks post gene transfer), vehicle-treated cMyBPC$^{-/-}$ hearts, and cMyBPC$^{-/-}$ fibers reconstituted with recombinant cMyBPC are summarized in Table 1. Skinned myocardial preparations were isolated from the region of the viral injection site in all groups of mice. There were no differences in in steady-state force generation at maximal and submaximal activating [Ca$^{2+}$] or in the steepness of the force-pCa relationship (Hill-coefficient, n$_H$) in any of the groups (FIG. 6). Consistent with previous studies, cMyBPC$^{-/-}$ skinned myocardium displayed dramatically accelerated rates of force development ($k_{tr}$) (FIG. 6), stretch-induced force decay ($k_{rel}$) and delayed force development ($k_{df}$) at submaximal Ca$^{2+}$-activations, and greater stretch-induced force decay (P$_2$ amplitude) and stretch activation amplitude (P$_{df}$), compared to WT myocardium (Table 2). Skinned myocardium isolated from LcMyBPC-treated cMyBPC$^{-/-}$ hearts displayed dramatically slower cross-bridge kinetics ($k_{tr}$, $k_{rel}$, and $k_{df}$) compared to untreated cMyBPC$^{-/-}$ myocardium, both 21 days and 20 weeks following cMyBPC gene transfer (Table 2, FIGS. 6 and 7). In contrast, skinned myocardium isolated from LCMV-treated cMyBPC$^{-/-}$ hearts, displayed similar stretch activation properties to untreated cMyBPC$^{-/-}$ myocardium (Table 2).

TABLE 2

Stretch activation parameters of skinned fibers isolated from WT and cMyBPC$^{-/-}$ hearts, following viral treatment.

| | $k_{df(s^{-1})}$ | $k_{rel(s^{-1})}$ | P$_2$ | P$_3$ | P$_{df}$ |
|---|---|---|---|---|---|
| WT (5) | 23.59 ± 1.23 | 271 ± 21 | 0.04 ± 0.01 | 0.10 ± 0.01 | 0.06 ± 0.01 |
| cMyBPC$^{-/-}$ (4) | 35.49 ± 1.40* | 470 ± 20* | −0.03 ± 0.01† | 0.10 ± 0.01 | 0.13 ± 0.01† |
| cMyBPC$^{-/-}$ + LCMV (3) | 34.96 ± 1.92* | 443 ± 32* | −0.04 ± 0.02† | 0.10 ± 0.02 | 0.14 ± 0.02† |
| cMyBPC$^{-/-}$ + LcMyBPC (21 days) (5) | 24.94 ± 1.79 | 280 ± 27 | 0.04 ± 0.02 | 0.11 ± 0.01 | 0.07 ± 0.02 |
| cMyBPC$^{-/-}$ + LcMyBPC (20 weeks) (3) | 26.03 ± 2.41 | 318 ± 36 | 0.04 ± 0.02 | 0.11 ± 0.02 | 0.07 ± 0.02 |

Data are means ± SE. Skinned ventricular fibers (20-25/group) was isolated from 3-5 mice per/group (indicated in parenthesis). All data presented for each sub-group was collected from the number of mice indicated in the left column. Rate constants were calculated from force transients in response to stretches of 1% of muscle length at ~half-maximal levels of activation. Stretch activation parameters are described in the data supplement. cMyBPC$^{-/-}$ + LCMV; vehicle-treated cMyBPC$^{-/-}$, cMyBPC$^{-/-}$ + LcMyBPC; LcMyBPC-treated cMyBPC$^{-/-}$ 21 days or 20 weeks following gene transfer.
*Significantly different from WT, P < 0.001.
†Significantly different from WT, P < 0.01.

The effects of increased exogenous cMyBPC content in cMyBPC$^{-/-}$ myocardium by in vivo gene transfer on contractile function were also directly compared to in vitro reconstitution of cMyBPC$^{-/-}$ myocardium with recombinant cMyBPC. Acute increases in cMyBPC content in the cMyBPC$^{-/-}$ sarcomere by in vivo and in vitro methods resulted in similar effects on contractile function, as incubation of cMyBPC$^{-/-}$ skinned myocardium with recombinant cMyBPC did not alter steady-state force generation (Table 1) but dramatically slowed cross-bridge kinetics such that they became indistinguishable from to WT myocardium (FIG. 6).

Effects of cMyBPC Gene Transfer on In Vivo Cardiac Function

Figure 9:
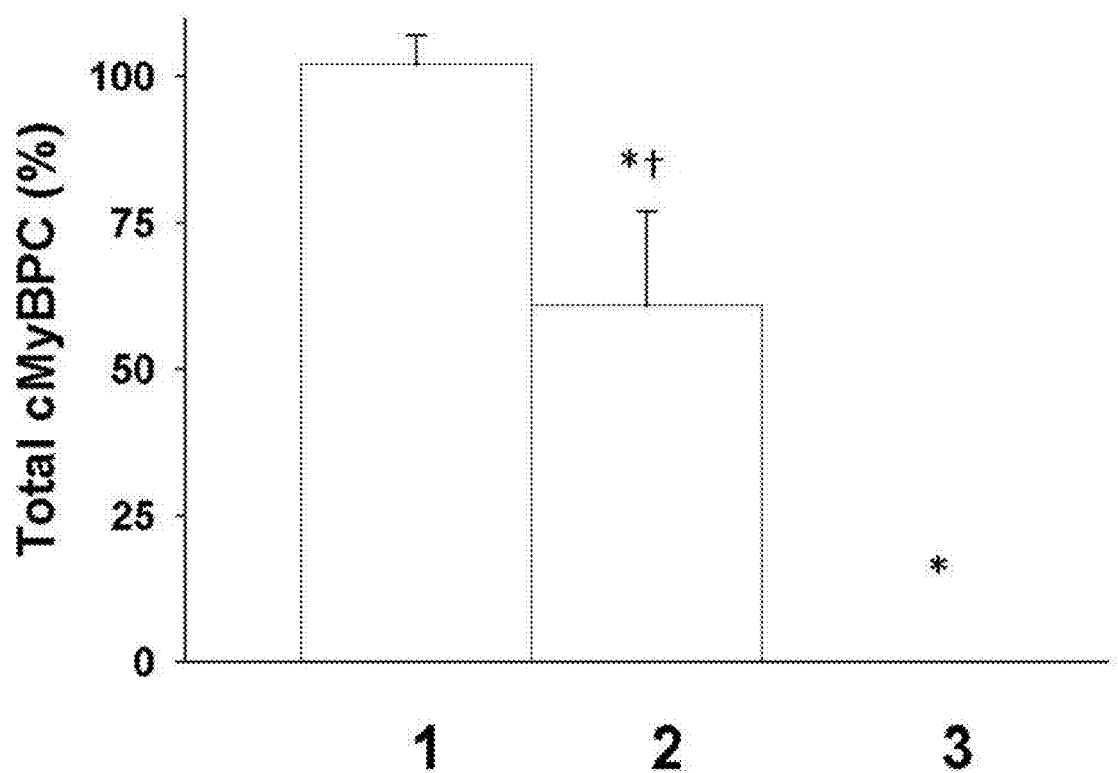
FIG. 9 illustrates a histogram showing total cMyBPC expression (normalized to α-actinin levels) as quantified by western blotting of LV homogenates of WT (lane 1), LcMyBPC treated cMyBPC$^{-/-}$ (lane 2), and cMyBPC$^{-/-}$ (lane 3) hearts that were studied by in vivo echocardiography. *Significantly different than WT, †significantly different than untreated cMyBPC$^{-/-}$.

The effects of cMyBPC gene transfer on in vivo cardiac contractile function were analyzed by echocardiography in a separate group of WT, cMyBPC$^{-/-}$, LcMyBPC-treated cMyBPC$^{-/-}$ mice, and are presented in Table 3. cMyBPC$^{-/-}$ hearts displayed significant increases in LV chamber dimensions at end-systole and end-diastole, as well increases in posterior wall thickness, and LV mass-to-bodyweight ratios compared to WT hearts (Table 3). Furthermore, cMyBPC$^{-/-}$ hearts displayed diminished fractional shortening and shortened systolic ejection time, and prolonged isovolumic relaxation times indicating impaired systolic and diastolic function, respectively (Table 3). As expected, vehicle-treated cMyBPC$^{-/-}$ hearts showed no differences in contractile function and LV morphology compared to untreated cMyBPC$^{-/-}$ hearts (data not shown), however, LcMyBPC-treated cMyBPC$^{-/-}$ hearts showed improvements in cardiac contractile function and reduced LV dimensions compared to untreated cMyBPC$^{-/-}$ hearts (Table 3, FIGS. 8-9). The effects of cMyBPC gene transfer on cMyBPC expression, in vivo cardiac contractility, and LV morphology of cMyBPC$^{-/-}$ hearts were variable. The average cMyBPC content of LcMyBPC-treated cMyBPC$^{-/-}$ hearts assessed by in vivo echocardiography was 60±17% of the cMyBPC content of WT hearts (range: 38-96%) (FIGS. 8-10). Hearts expressing high levels of cMyBPC displayed contractile function and LV wall dimensions that were similar to WT hearts (FIGS. 8-10), whereas hearts expressing cMyBPC at lower levels showed some functional improvements but modest changes in wall dimensions. Overall, averaged data for all LcMyBPC treated hearts (N=19) showed statistically significant improvements in contractile function and cardiac morphology compared with untreated cMyBPC$^{-/-}$ hearts (Table 3).

TABLE 3

In vivo echocardiography summary data from WT and cMyBPC$^{-/-}$ mice.

| | WT | cMyBPC$^{-/-}$ | cMyBPC$^{-/-}$ + LcMyBPC |
|---|---|---|---|
| | | Number of mice | |
| | 14 | 14 | 19 |
| BW (g) | 31.13 ± 2.30 | 29.89 ± 0.33 | 30.03 ± 1.37 |
| HR (beats/min) | 435 ± 8 | 443 ± 7 | 433 ± 13 |
| PWTd (mm) | 0.86 ± 0.03 | 1.15 ± 0.03* | 1.01 ± 0.05‡§ |
| PWTs (mm) | 1.26 ± 0.03 | 1.52 ± 0.05† | 1.39 ± 0.06‡ |
| EDD (mm) | 3.47 ± 0.12 | 4.50 ± 0.10† | 3.90 ± 0.20‡ |
| ESD (mm) | 1.65 ± 0.11 | 3.10 ± 0.08* | 2.19 ± 0.17‡§ |
| LVM/BM (mg/g) | 3.28 ± 0.19 | 6.54 ± 0.23* | 4.74 ± 0.62†# |
| FS | 0.52 ± 0.02 | 0.31 ± 0.02* | 0.44 ± 0.04‡§ |
| ET (ms) | 65.88 ± 2.67 | 47.16 ± 2.19* | 58.04 ± 3.80§ |
| IVRT (ms) | 22.74 ± 3.06 | 39.21 ± 3.02† | 29.08 ± 3.99‡§ |

All values are expressed as means ± SE.
HR = heart rate,
PWTd = left ventricular posterior wall thickness diameter in diastole,
PWTs = LV posterior wall thickness diameter in diastole in systole,
EDD = end-diastolic LV dimension,
ESD = end-systolic LV dimension,
LVM/BM = LV mass/body mass,
FS = endocardial fractional shortening,
ET = ejection time,
IVRT = isovolumic relaxation time.
cMyBPC$^{-/-}$ + LcMyBPC; cMyBPC treated cMyBPC$^{-/-}$ 21 days following gene transfer.
*Significantly different from WT, P < 0.001.
†Significantly different from WT, P < 0.01.
‡Significantly different from WT, P < 0.05.
Significantly different from cMyBPC$^{-/-}$, P < 0.01.
§Significantly different from cMyBPC$^{-/-}$, P < 0.05.

The expression and localization of cMyBPC in the myocardium of LcMyBPC-treated cMyBPC⁻/⁻ hearts was further analyzed by immunohistochemistry in serial sections cut from the apex, mid-LV, and base. LcMyBPC-treated hearts which showed significant improvements in in vivo function, exhibited robust cMyBPC expression (FIG. 8-10) throughout the myocardium even in regions of the LV distal from the injection site, whereas in LcMyBPC-treated hearts which did not show marked improvements in in vivo function, cMyBPC expression was mostly localized to regions proximal to the viral injection site, and was usually absent in the distal base region (data not shown).

From the above description of the invention, those skilled in the art will perceive improvements, changes and modifications. Such improvements, changes and modifications within the skill of the art are intended to be covered by the appended claims. All patents, patent applications and publications cited herein are incorporated by reference in their entirety.

I claim:

1. A method of treating cardiomyopathy in a subject, the method comprising administering to the subject a therapeutically effective amount of an agent that modulates contractile function in a myocardial tissue of the subject, the agent comprising a vector that includes a nucleic acid encoding a cMyBPC protein or a mutant cMyBPC protein thereof, wherein the mutant cMyBPC protein includes a triple S to D phosphorylation mutation and accelerates contraction in myocardial tissue of the subject or a triple S to A phosphorylation mutation and decreases contraction in myocardial tissue of the subject.

2. The method of claim 1, the myocardial tissue comprising left ventricle cardiac tissue.

3. The method of claim 1, the agent being administered directly to the myocardial tissue of the subject.

4. The method of claim 1, the agent being administered to the subject's myocardial tissue at an amount effective to cause functional improvement in at least one of left ventricular end systolic volume, left ventricular ejection fraction, wall motion score index, left ventricular end diastolic length, left ventricular end systolic length, left ventricular end diastolic area, left ventricular end systolic area, or left ventricular end diastolic volume.

* * * * *